United States Patent
Lee et al.

(10) Patent No.: US 10,814,010 B2
(45) Date of Patent: Oct. 27, 2020

(54) FOXC2 INHIBITOR AND METHODS OF USE THEREOF

(71) Applicants: The Board of Regents of The University of Texas System, Austin, TX (US); Pohang University Of Science and Technology, Pohang (KR)

(72) Inventors: Jiyong Lee, Richardson, TX (US); Hyun-Suk Lim, Pohang (KR); Maria Castaneda, Garland, TX (US)

(73) Assignees: The Board of Regents, The University of Texas System, Austin, TX (US); Pohang University of Science and Technology, Pohang (KR)

( * ) Notice: Subject to any disclaimer, the term of this patent is extended or adjusted under 35 U.S.C. 154(b) by 0 days.

(21) Appl. No.: 16/363,335

(22) Filed: Mar. 25, 2019

(65) Prior Publication Data
US 2019/0290774 A1    Sep. 26, 2019

Related U.S. Application Data

(60) Provisional application No. 62/647,317, filed on Mar. 23, 2018.

(51) Int. Cl.
| | |
|---|---|
| *C07D 413/14* | (2006.01) |
| *A61K 47/68* | (2017.01) |
| *A61P 35/04* | (2006.01) |
| *A61K 31/5377* | (2006.01) |

(52) U.S. Cl.
CPC ...... *A61K 47/6803* (2017.08); *A61K 31/5377* (2013.01); *A61P 35/04* (2018.01); *C07D 413/14* (2013.01)

(58) Field of Classification Search
CPC .................................................. C07D 413/14
See application file for complete search history.

(56) References Cited

PUBLICATIONS

Castaneda, Maria, et al. "A Forkhead Box Protein C2 Inhibitor: Targeting Epithelial-Mesenchymal Transition and Cancer Metastasis." *Chembiochem* 19.13 (2018): 1359-1364.

Oh, Misook, et al. "Potential pharmacological chaperones targeting cancer-associated MCL-1 and Parkinson disease-associated α-synuclein." *Proceedings of the National Academy of Sciences* 111.30 (2014): 11007-11012.

*Primary Examiner* — Bruck Kifle
(74) *Attorney, Agent, or Firm* — Parker Highlander PLLC

(57) ABSTRACT

In one aspect, the present disclosure provides a compound of the formula:

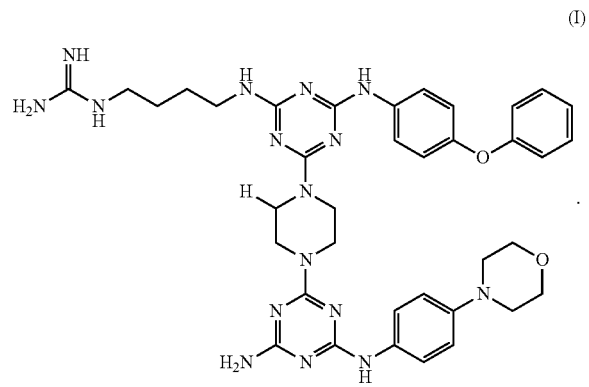

In another aspect, the present disclosure also provides methods of preparing the compound disclosed herein. In another aspect, the present disclosure also provides pharmaceutical compositions and methods of use of the compound disclosed herein. Additionally, methods of treating cancer with the compound disclosed herein are described.

15 Claims, 31 Drawing Sheets
(24 of 31 Drawing Sheet(s) Filed in Color)

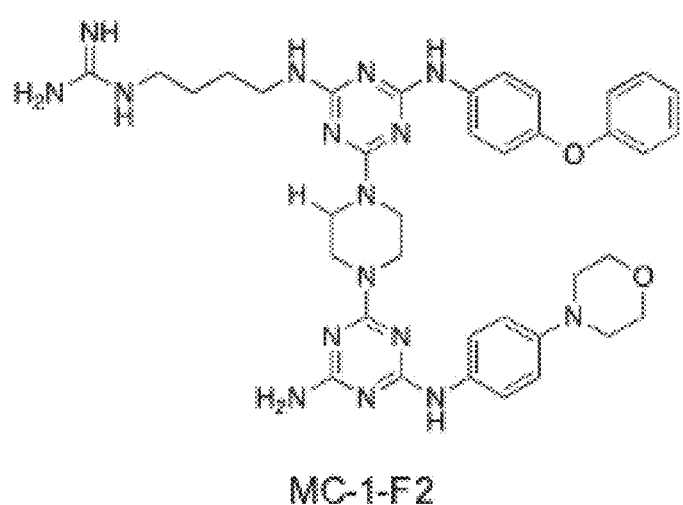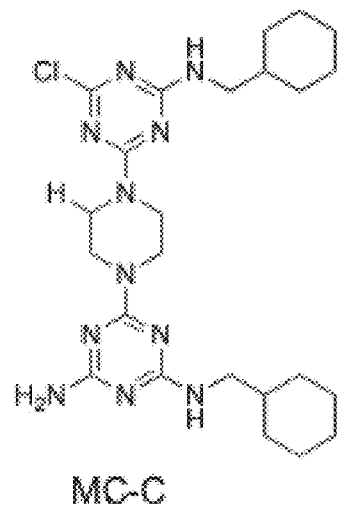
MC-1-F2　　　　　　MC-C
FIG. 1

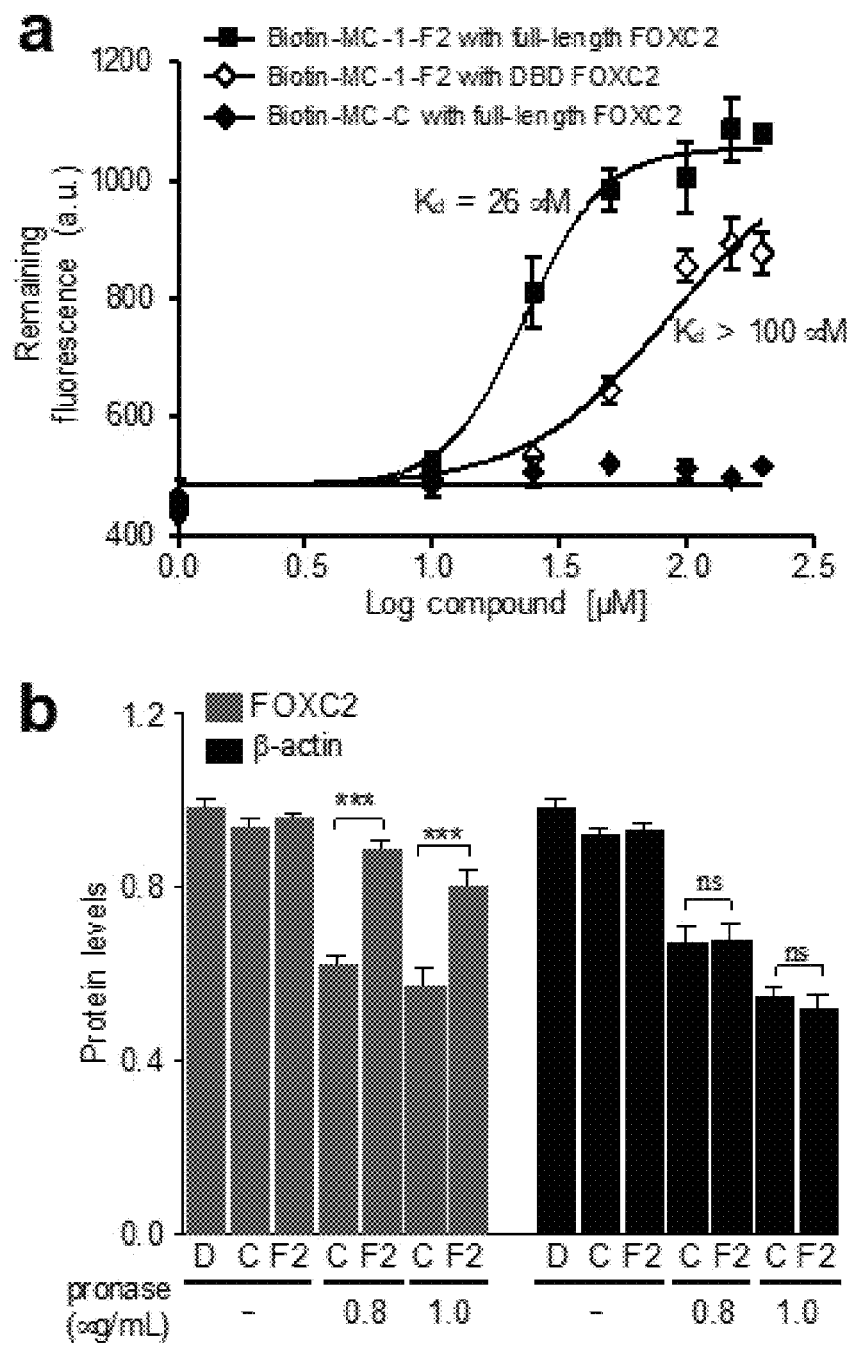
FIGS. 2A-B

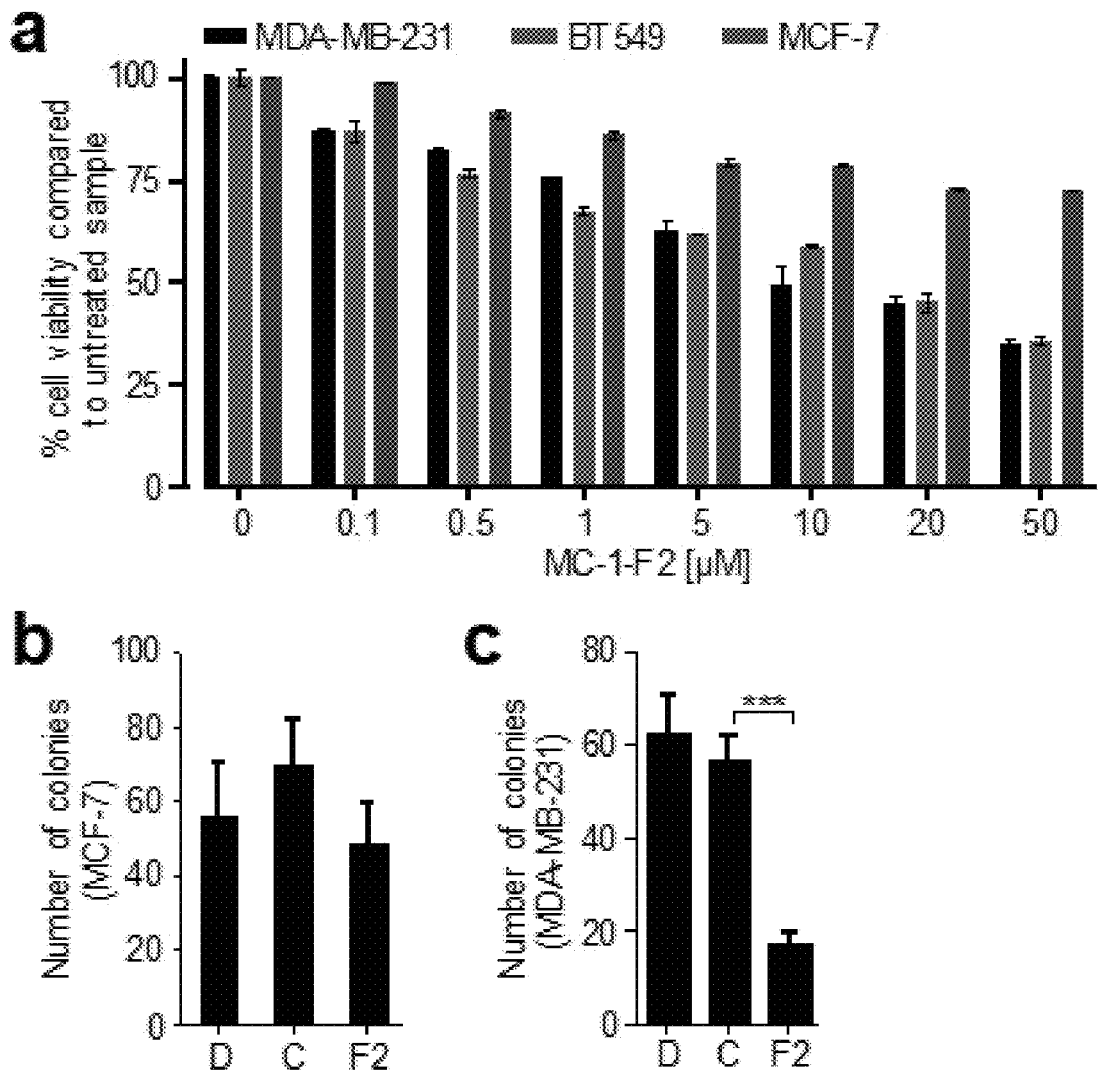
FIGS. 3A-C

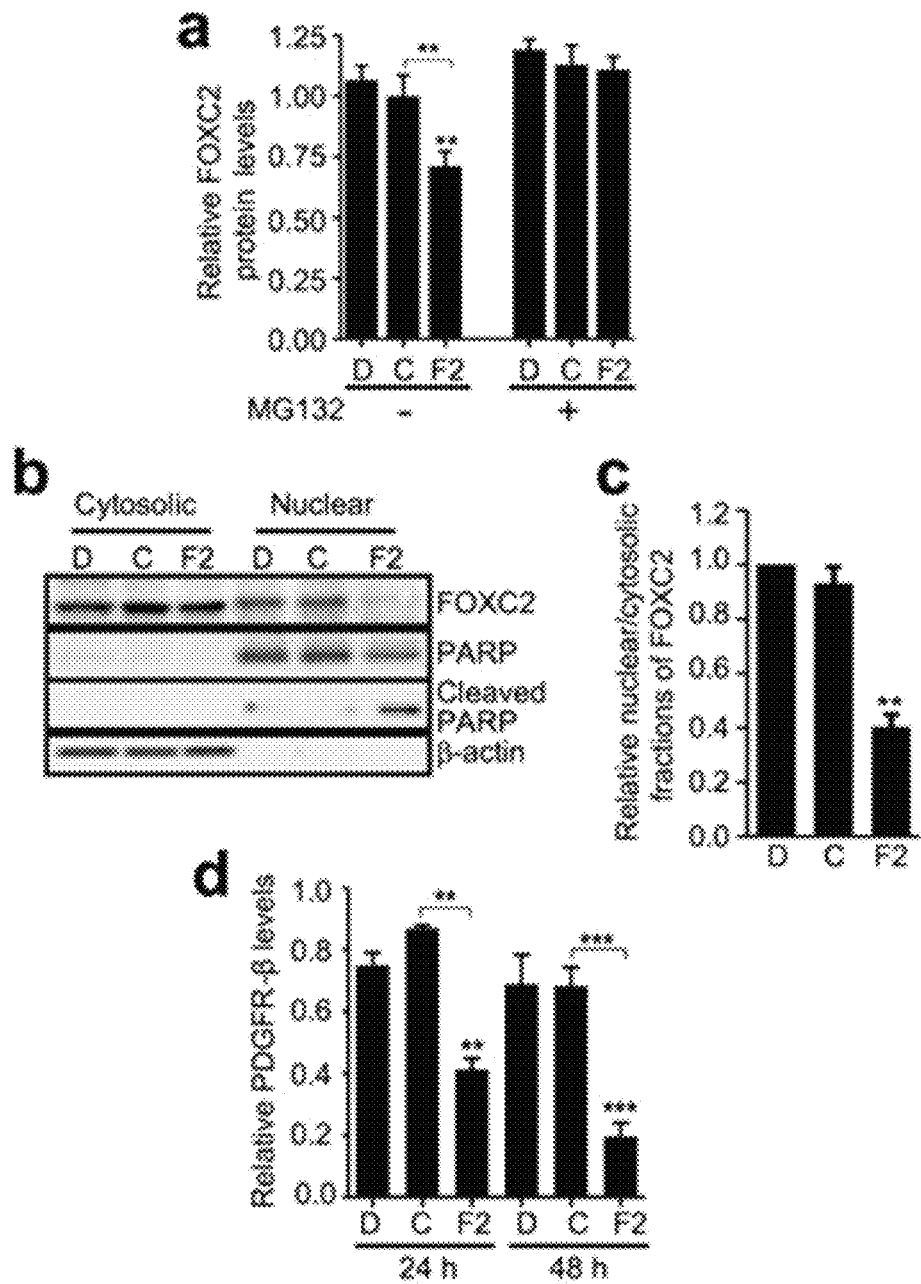
FIGS. 4A-D

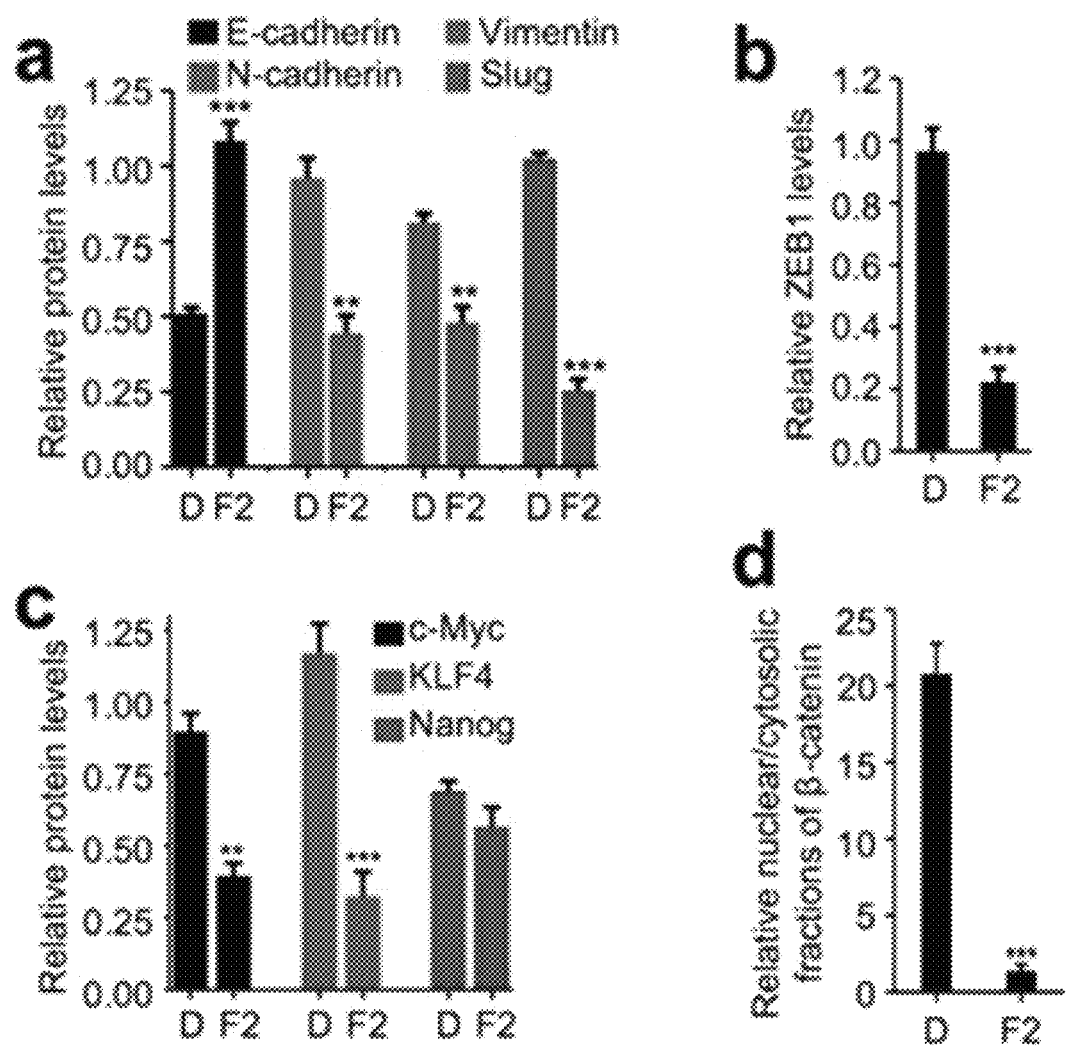
FIGS. 5A-D

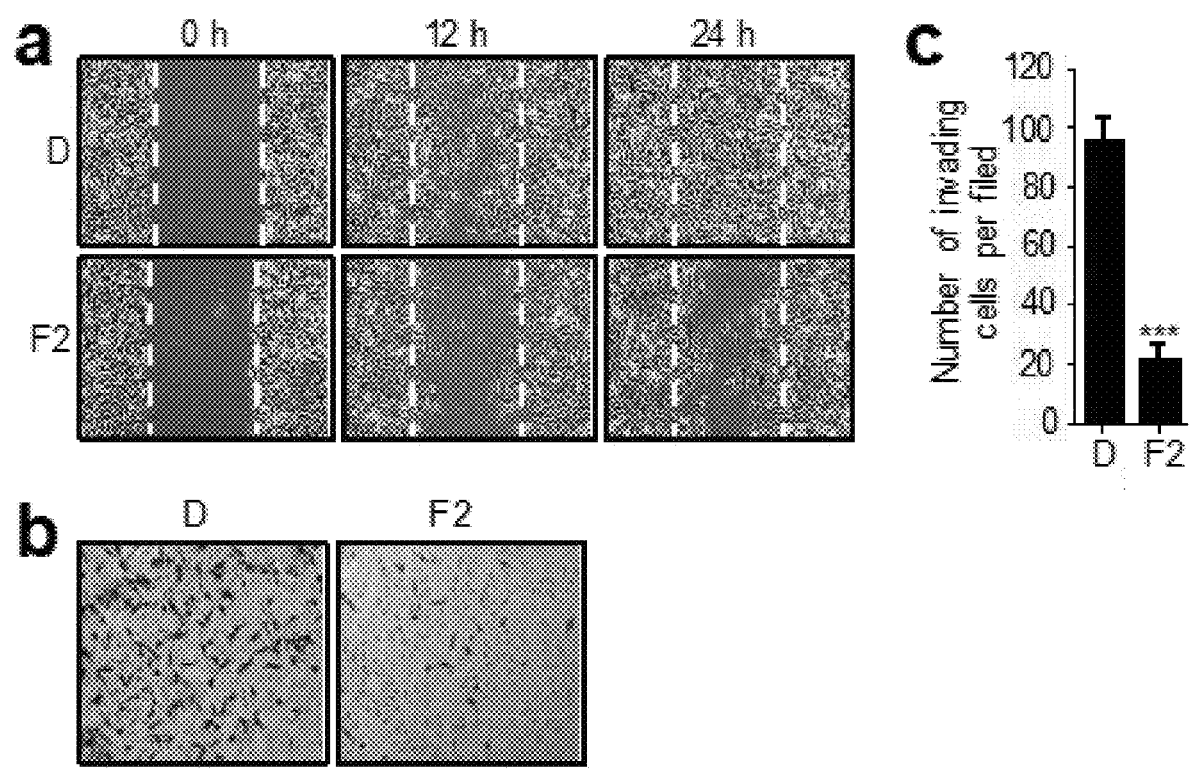
FIGS. 6A-C a
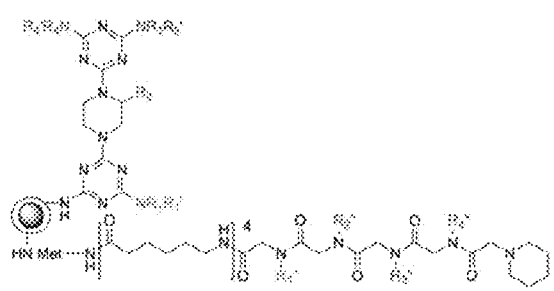
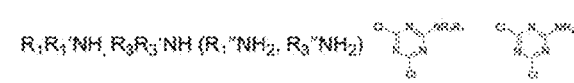
b  $R_1R_1'NH, R_3R_3'NH (R_1''NH_2, R_3''NH_2)$
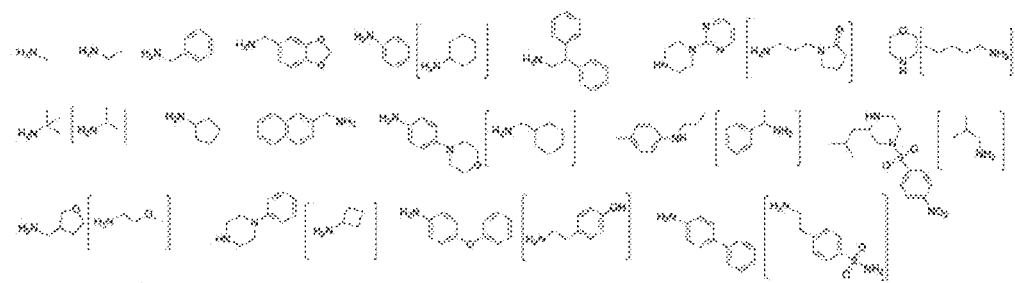
$R_2 (R_2''NH_2)$
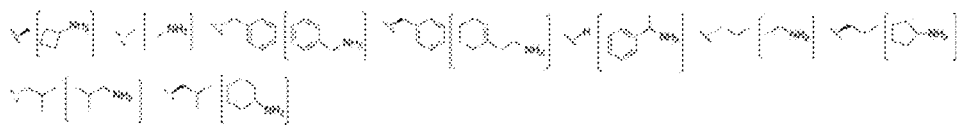
$R_4R_4'NH (R_4''NH_2)$
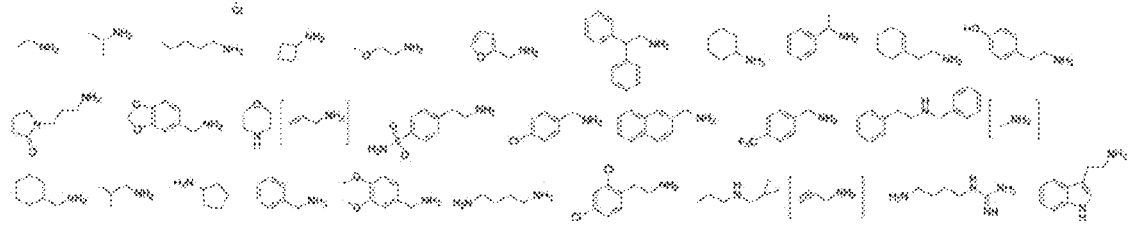
FIGS. 7A-B

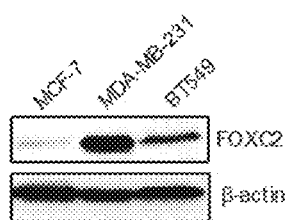
FIG. 13
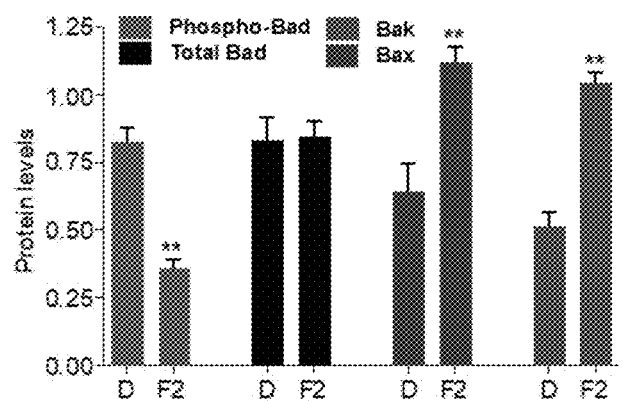
FIG. 14
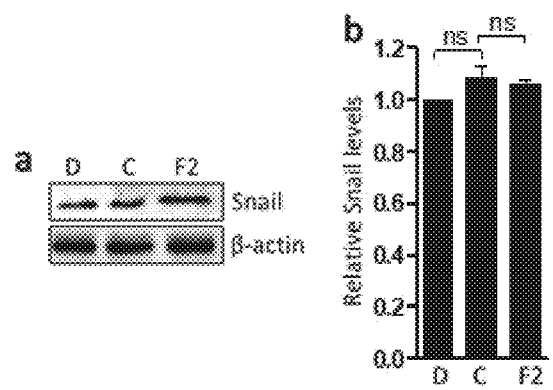
FIGS. 15A-B

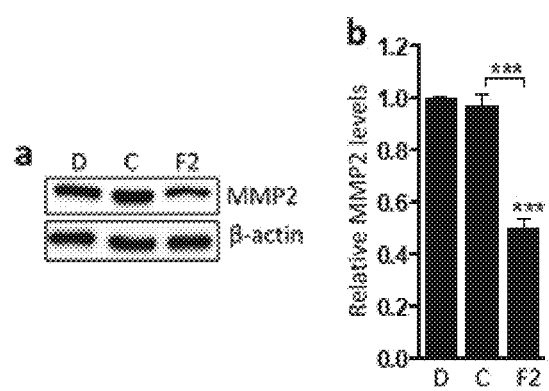
FIGS. 16A-B
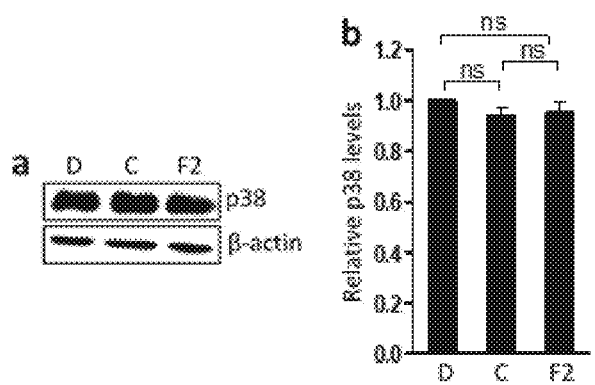
FIGS. 17A-B

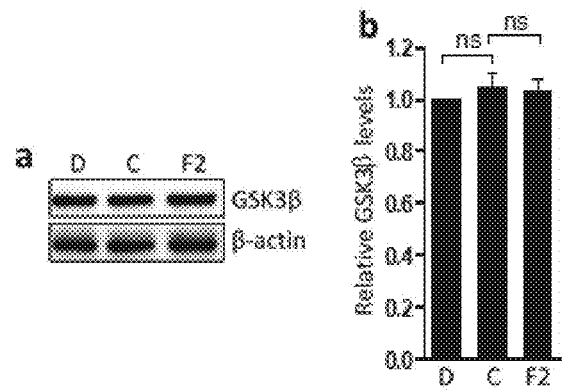
FIGS. 18A-B
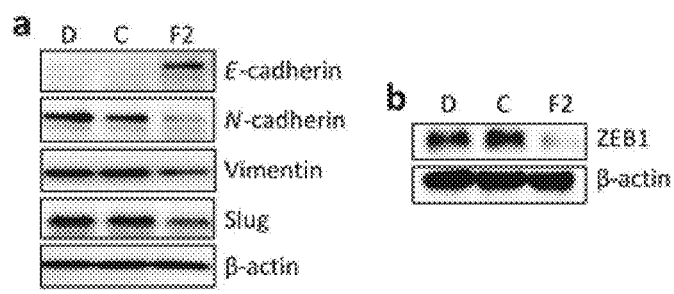
FIGS. 19A-B
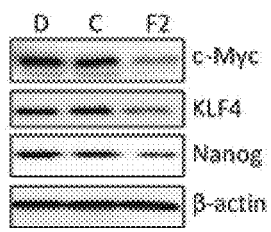
FIG. 20

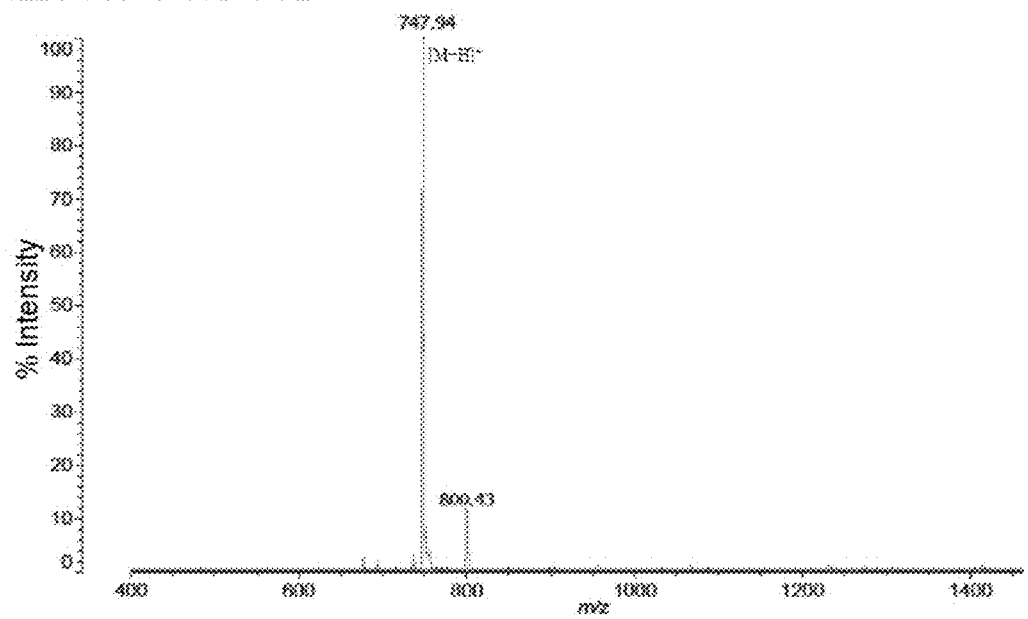
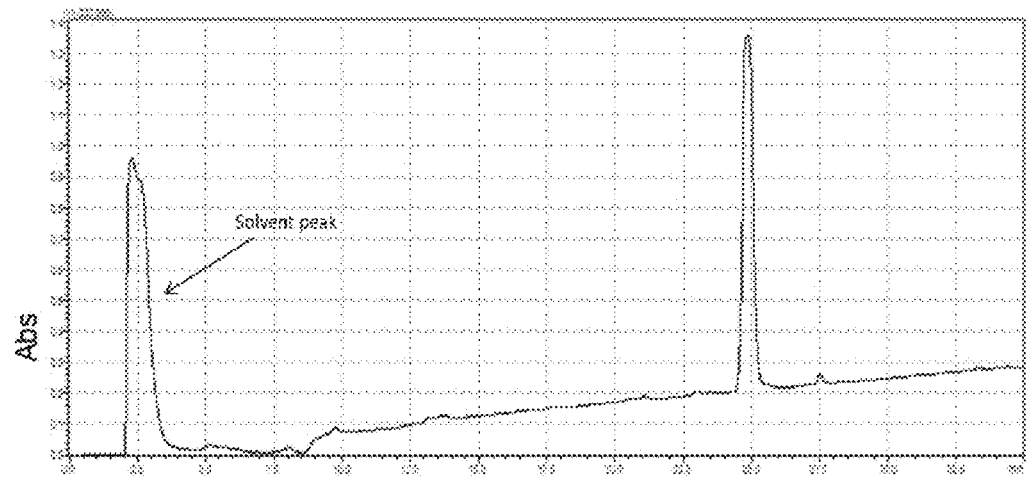
FIG. 24A

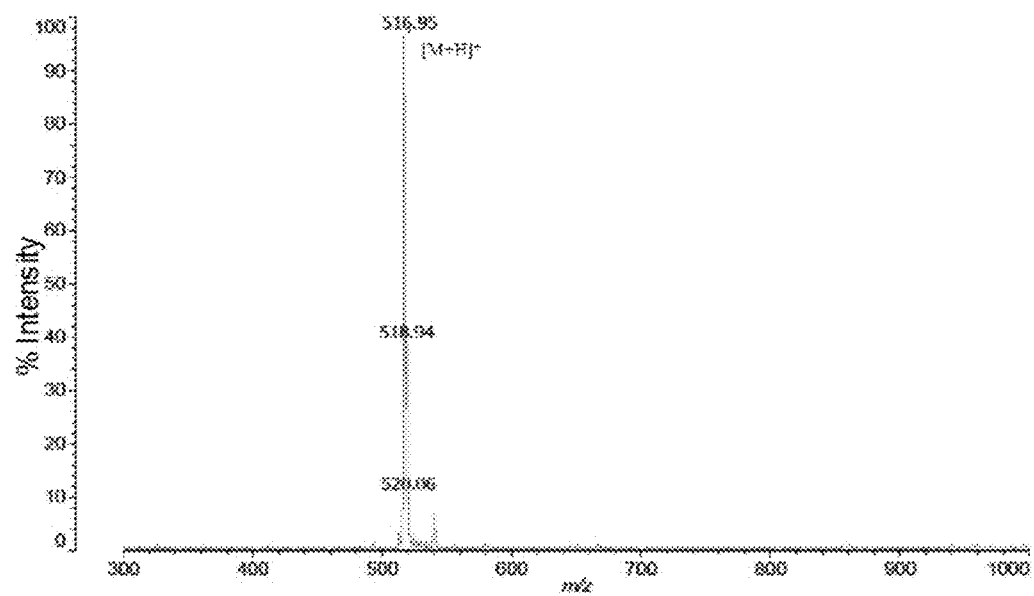
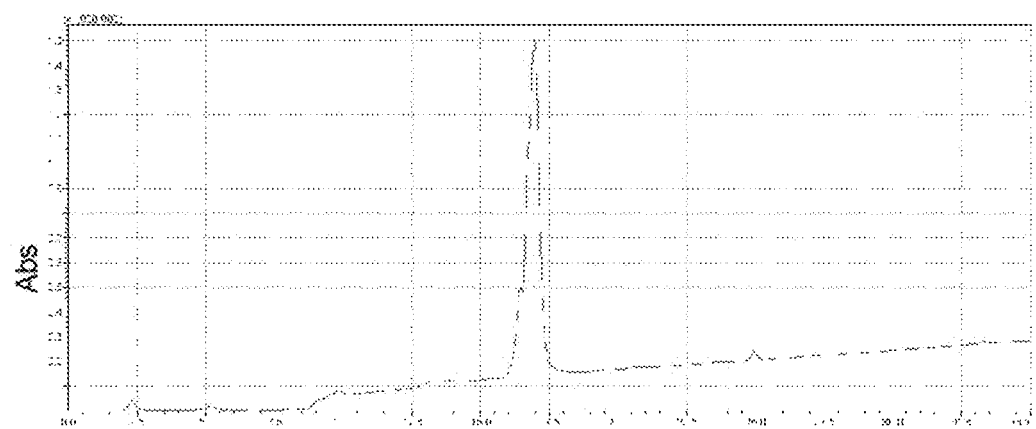
FIG. 24B

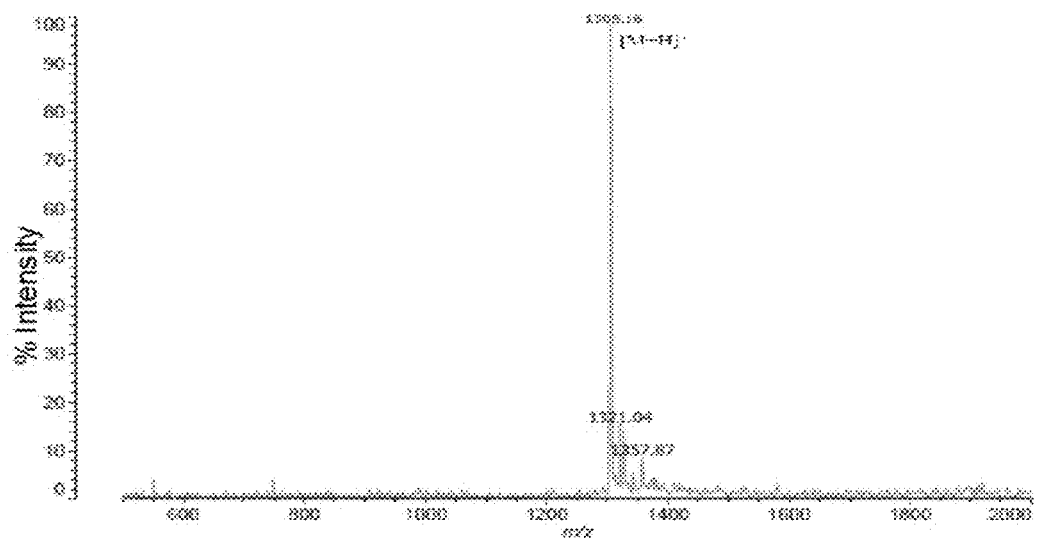
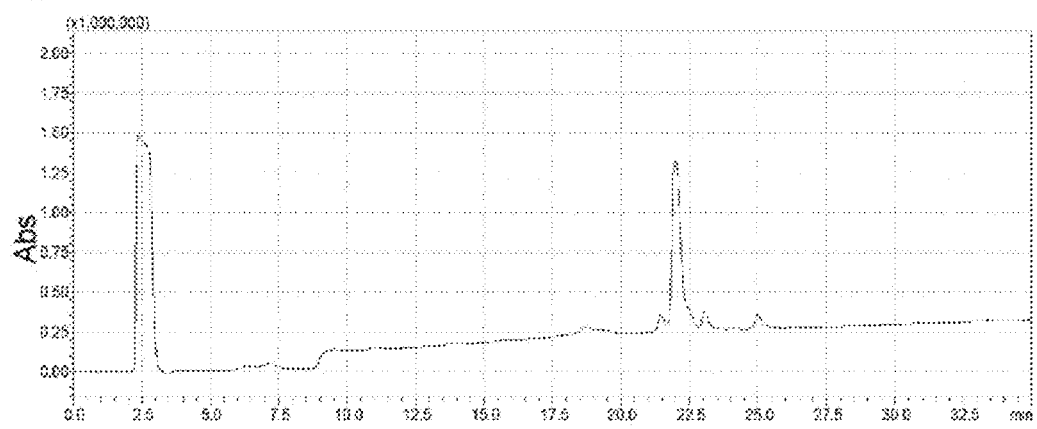
FIG. 24C

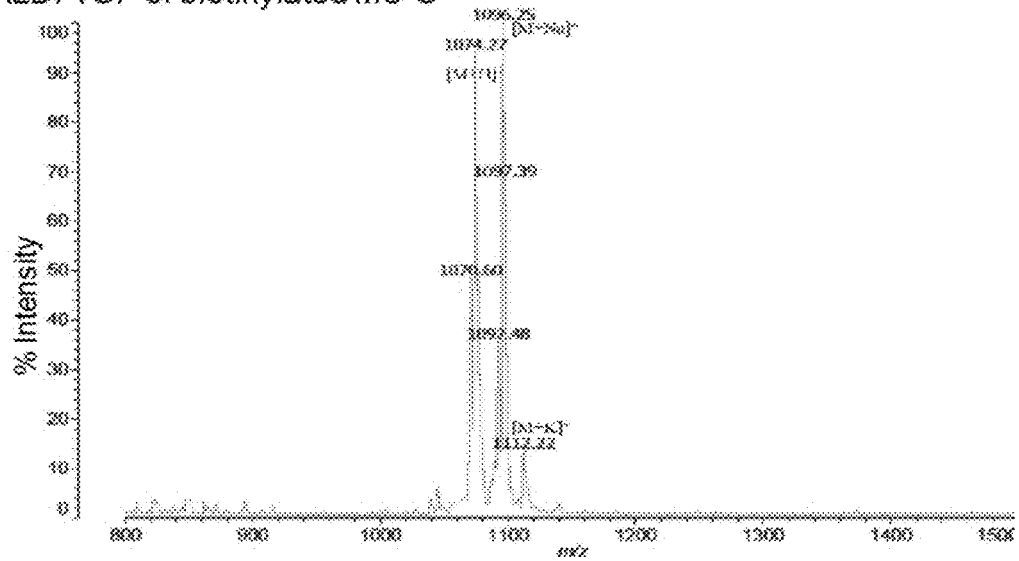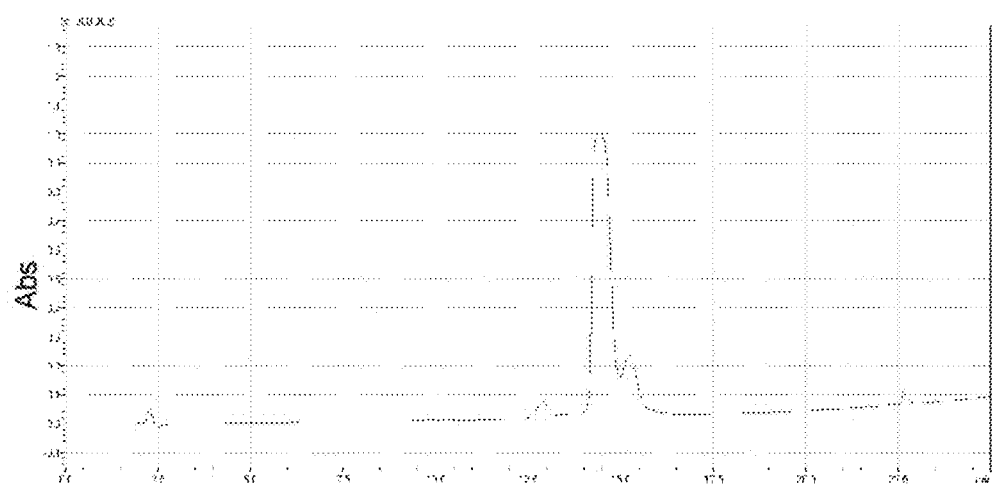
FIG. 24D

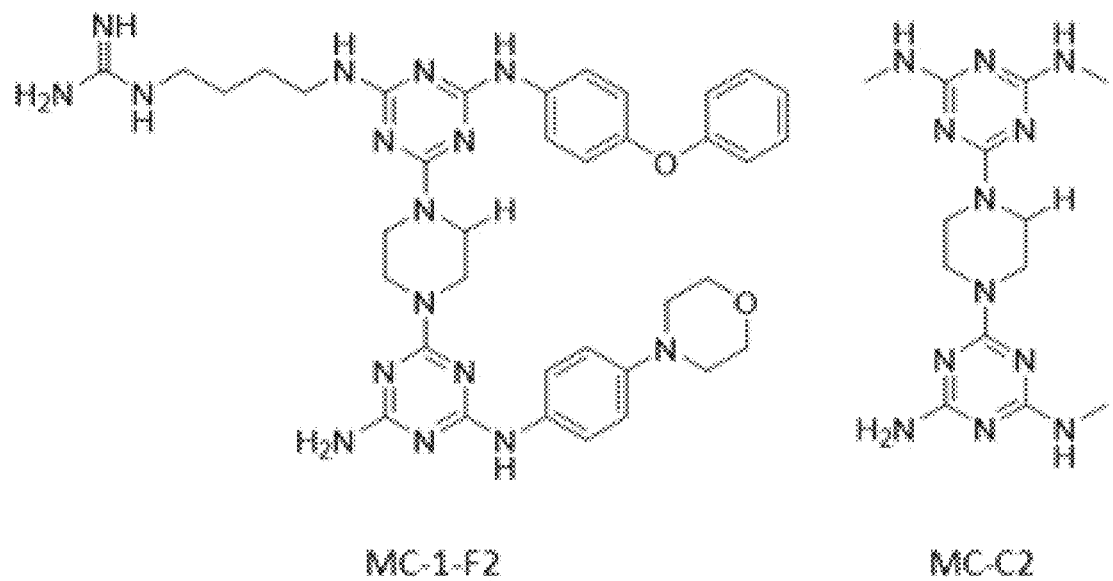
FIG. 25
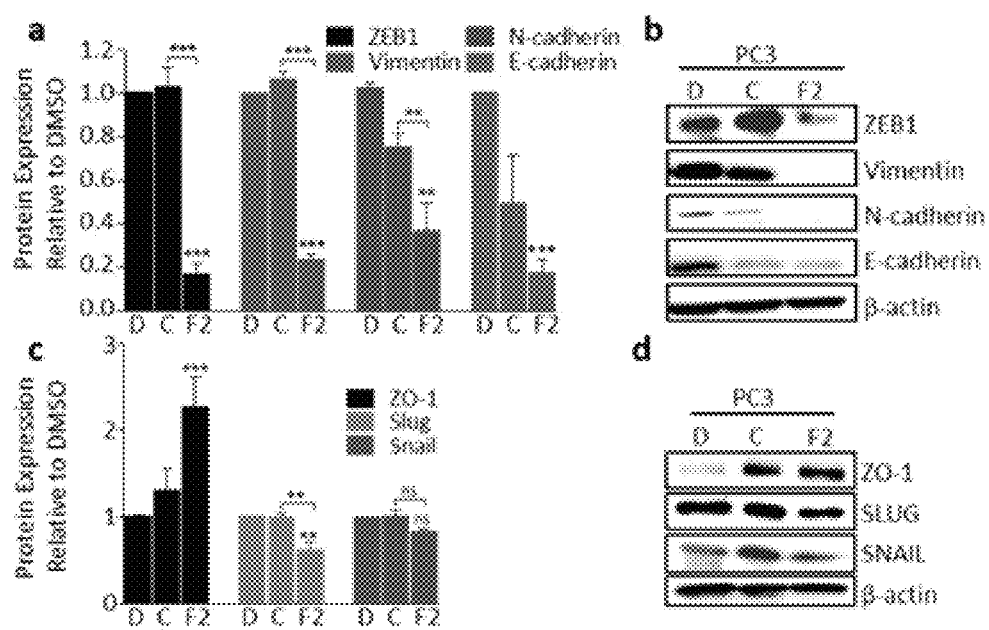
FIGS. 26A-D

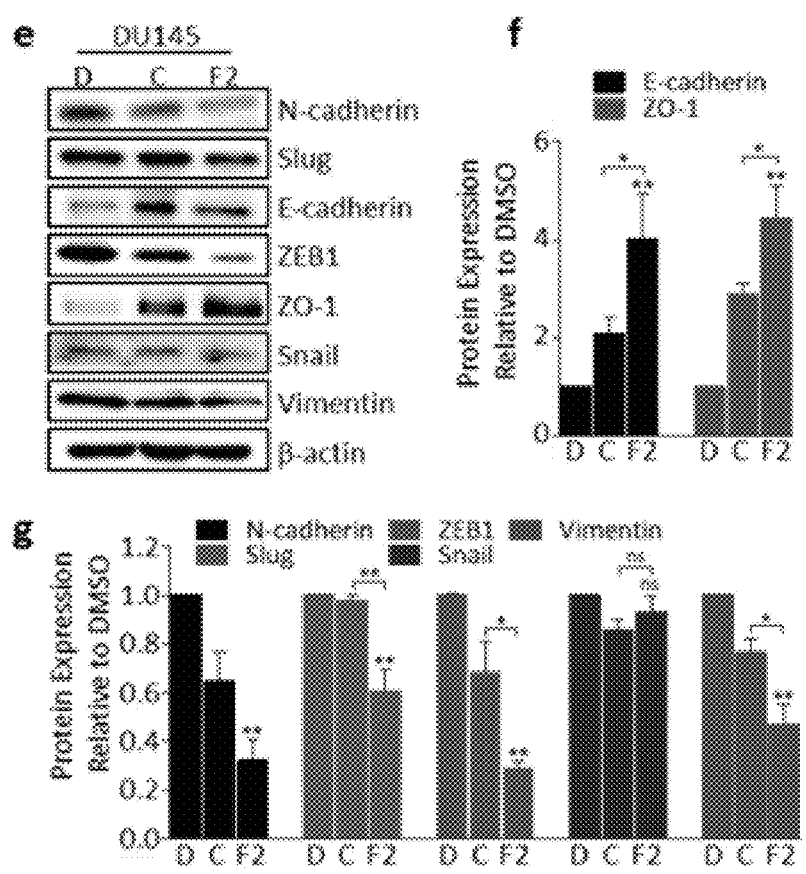
FIGS. 26E-G

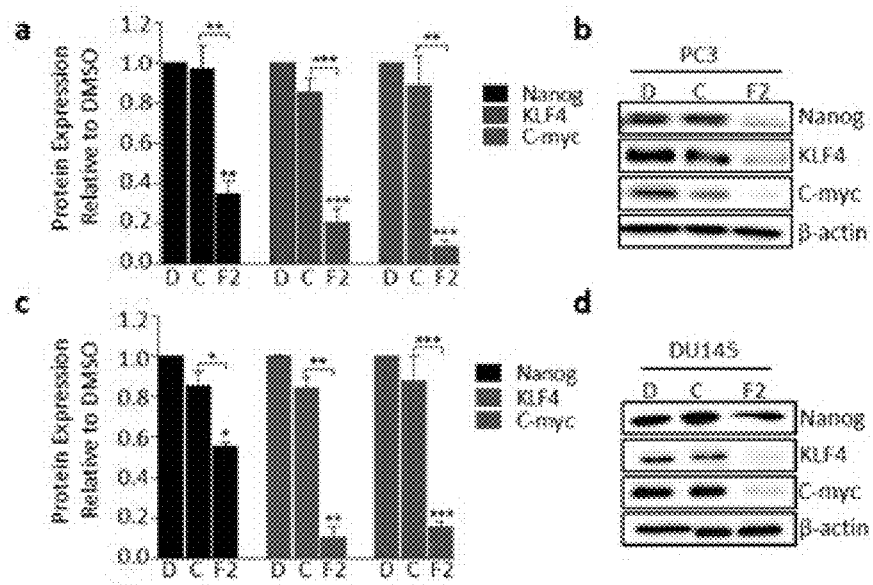
FIGS. 27A-D
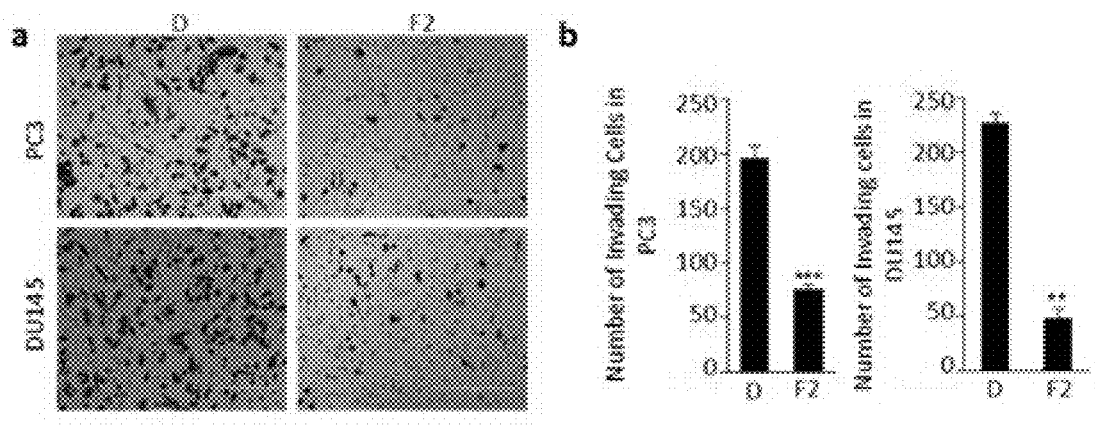
FIGS. 28A-B

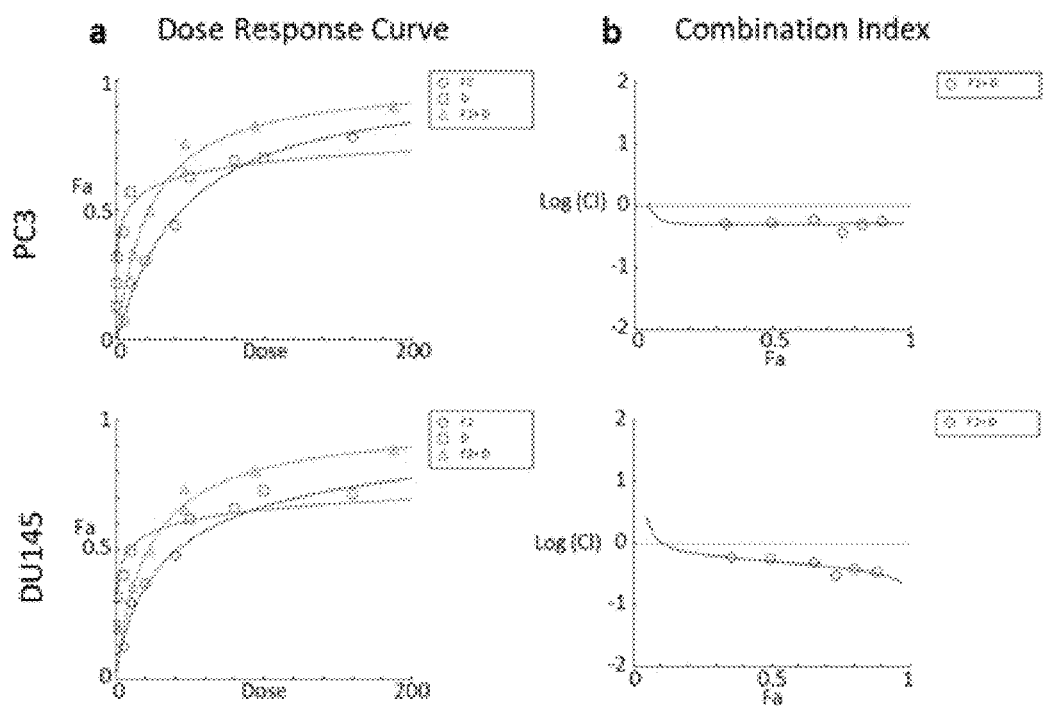
FIGS. 29A-B
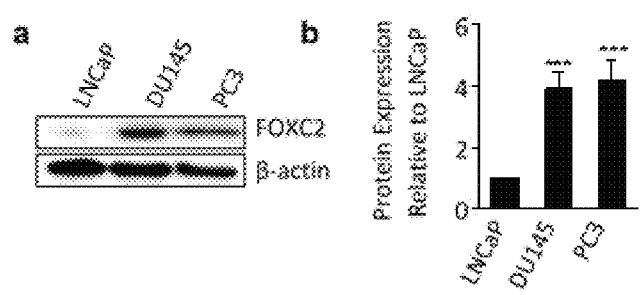
FIGS. 30A-B

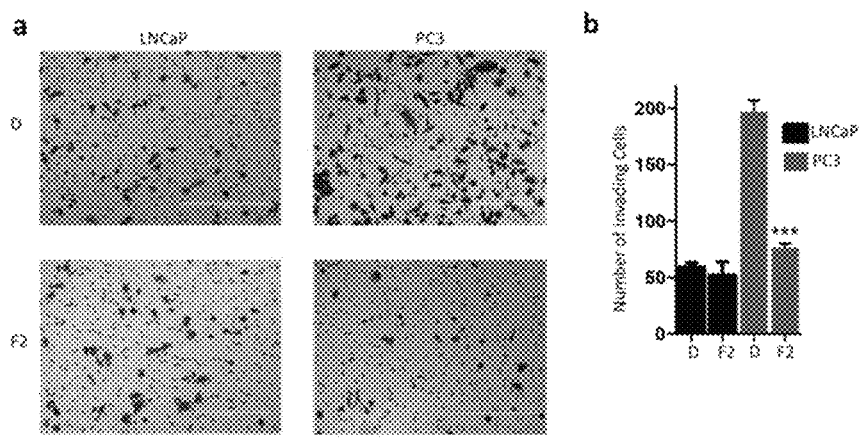
FIGS. 31A-B
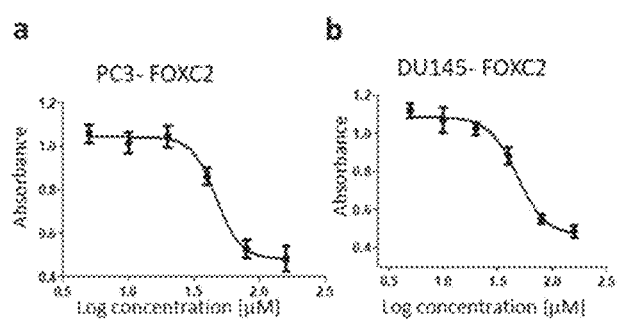
FIGS. 32A-B

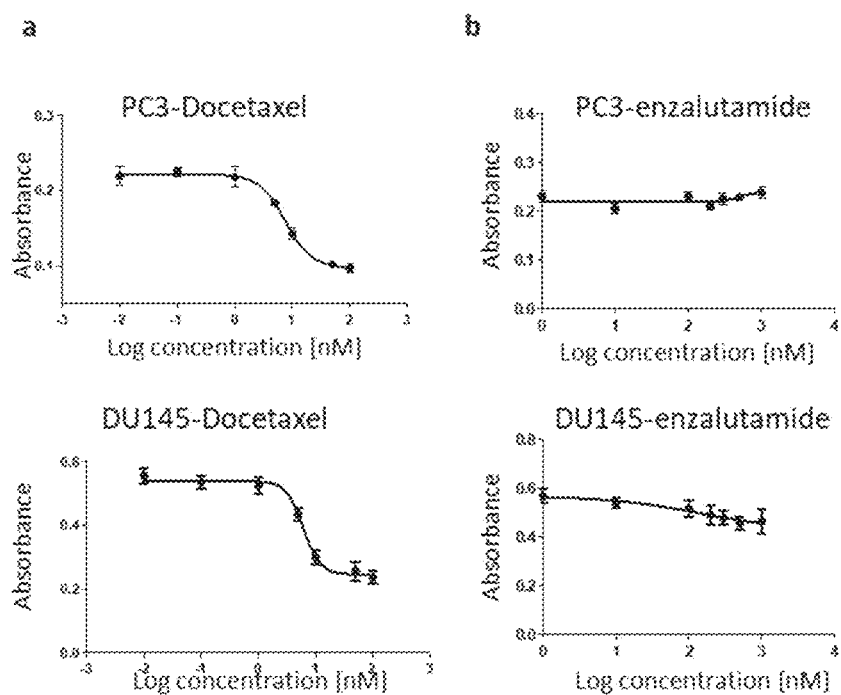
FIGS. 33A-B
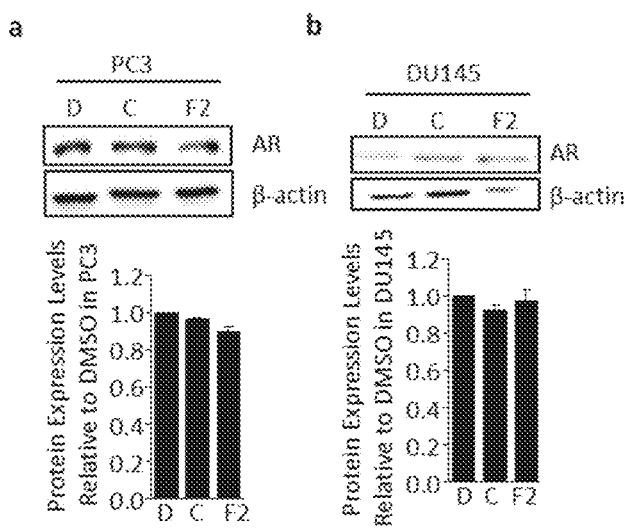
FIGS. 34A-B

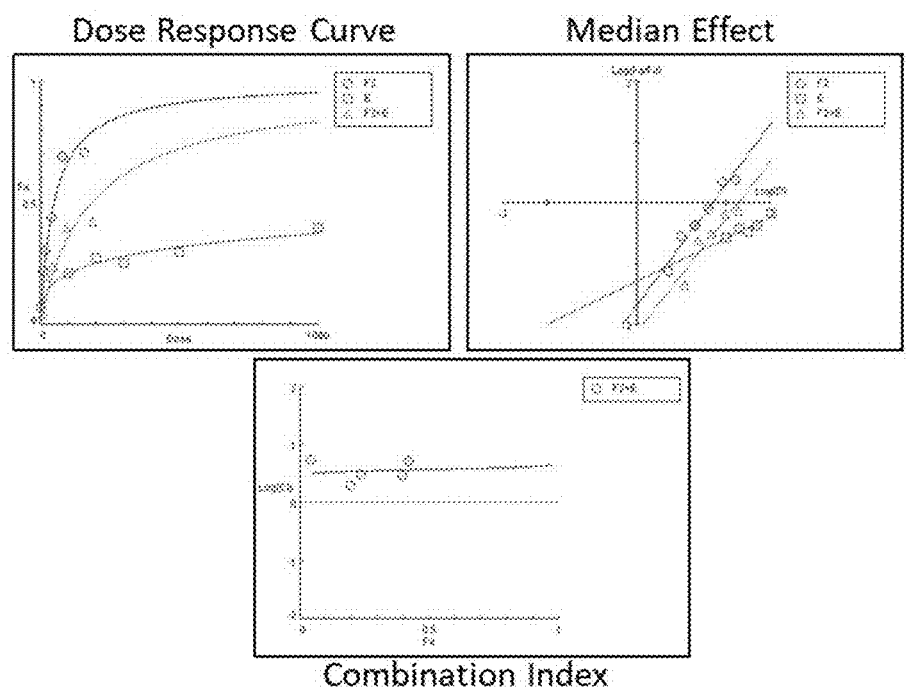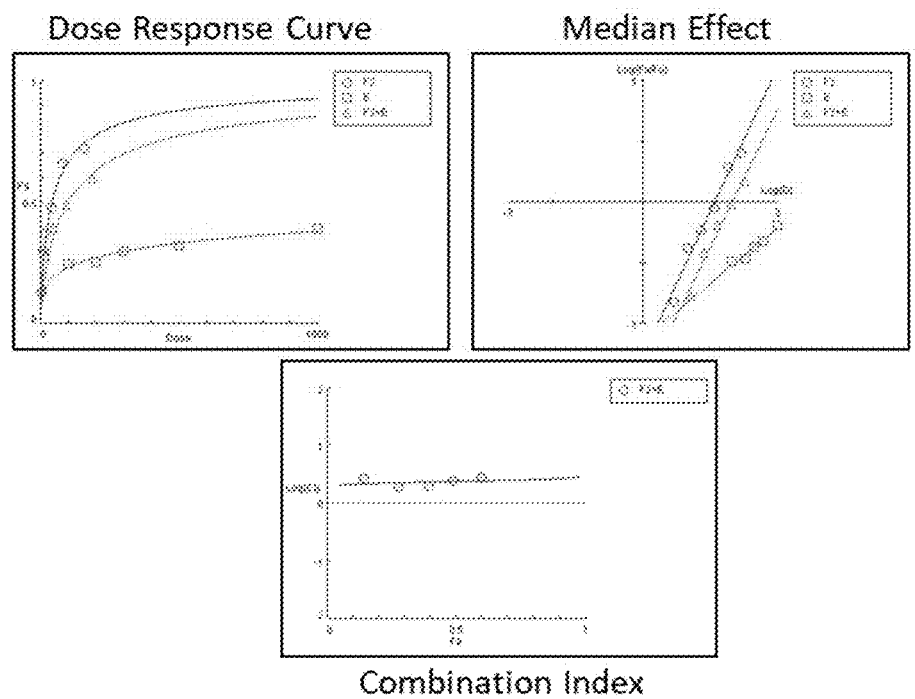
FIGS. 35A-B

FOXC2 INHIBITOR AND METHODS OF USE THEREOF

REFERENCE TO RELATED APPLICATIONS

The present application claims the priority benefit of U.S. provisional application No. 62/647,317, filed Mar. 23, 2018, the entire contents of which is incorporated herein by reference.

BACKGROUND

1. Field

This disclosure relates to the fields of medicine, pharmacology, chemistry, and oncology. In particular, a new compound, pharmaceutical compositions and methods of treatment using the same are disclosed.

2. Description of Related Art

Prostate Cancer is one of the top five most diagnosed cancers worldwide, with androgen deprivation therapy (ADT) as the common prescribed treatment for advanced prostate cancer. However, ADT therapy leads to the acquisition of androgen-independent mechanisms. This resistance to ADT leads to what is known as castration resistant prostate cancer (CRPC), with about 90% of patients diagnosed progressing to this stage. This stage of cancer progression is associated with distant metastasis, androgen independence, and resistance to common chemotherapeutic agents such as docetaxel. These characteristics lead to high mortality rates with survival rates of 1-2 years after recurrence or metastatic lesion detection.

Current research into treatments of CRPC aim at targeting the epithelial-mesenchymal transition (EMT). EMT leads to the breakdown of cell-cell contact, acquisition of cancer stem cell like characteristics, increase invasive capabilities and increase in chemoresistance. EMT has emerged as a target for CRPC as most mortality associated events are due to distant metastasis. It has been suggested by a number of researchers that androgen maintenance is necessary for EMT regulation, with androgen deprivation leading to androgen independence causing an initiation of EMT. Thus, the main treatment of prostate cancer, ADT therapy leads to EMT initiation and progression into CRPC.

Alternatives to ADT therapy for prostate cancer focus on the use of chemotherapeutic agents such as docetaxel. However, as stated before, chemoresistance develops over time. Chemoresistance in EMT is governed by the transcription factor ZEB1, which is governed by FOXC2. The transcription factor FOXC2, has been previously shown to a central regulator of EMT, with FOXC2 being necessary for the maintenance and initiation of EMT. It has also been shown that high FOXC2 levels are associated with CRPC, as well as vital in the induction of ADT resistance. The inhibition of FOXC2 was shown to inhibit EMT progression, render cells more susceptible to docetaxel, and lead to a decrease in cancer stem cell characteristics.

Similarly, patients diagnosed with aggressive forms of breast cancer will face the possibility of metastasis and low survival rates. EMT has been thought to be at the forefront of cancer metastasis, identified as a key event in cancer invasion. EMT is a process in which epithelial cells undergo a transition that causes cells to become mesenchymal. At the basis of EMT lies the dissolution of cell polarity and cell junctions. This loss of cell junctions leads to the loss of E-cadherin and acquisition of N-cadherin, a hallmark of EMT. EMT is known to be regulated by EMT-associated transcription factors, Snail, Slug, Twist, Goosecoid, ZEB1 and FOXC2. It has also been shown that EMT progression leads to the acquisition of cancer stem cell (CSC) properties. CSC is a small subpopulation of cells in tumors that express traits similar to those of stem cells, primarily the ability to self-renew and generate a heterogeneity of cells. CSC displays a higher tumor initiating ability as well as chemoresistance and ability to evade immunosurveillance. It is these CSC-like traits that give metastatic cells a more aggressive and metastatic phenotype.

New drugs for use in inhibiting EMT, and treating these challenging cancers are therefore urgently needed.

SUMMARY

In some aspects, the present disclosure provides a compound having the formula:

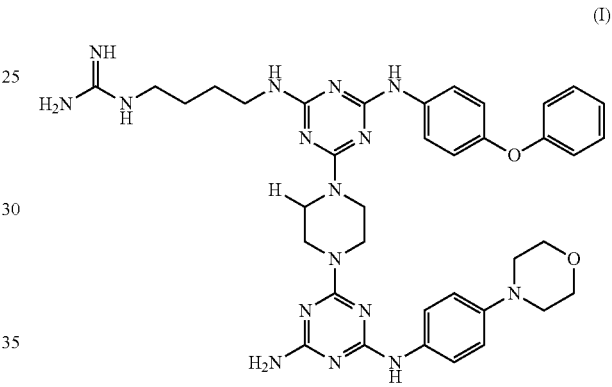

or a pharmaceutically acceptable salt thereof. Also provided is a pharmaceutical composition comprising a compound according to claim 1 and an excipient. The pharmaceutical composition may be formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

In another aspect, there is provided a method of treating cancer in a patient in need thereof comprising administering to the patient a therapeutically effective amount of a compound or composition as disclosed above. The cancer may be is a carcinoma, sarcoma, lymphoma, leukemia, melanoma, mesothelioma, multiple myeloma, or seminoma. The cancer may be one of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In particular, the cancer may be breast cancer or prostate cancer, such as drug-resistant breast cancer, or castration-resistant prostate cancer.

The method may further comprise administering a second therapy, such as surgery, a second chemotherapeutic, radiotherapy, or immunotherapy. The method patient may be a mammal, such as a human or non-human mammal. The compound may be administered once, or be administered two or more times, such as being administered chronically.

In another aspect, there is provided a method of reversing epithelial-mesenchymal transition (EMT) in a cancer patient in need thereof comprising administering to the patient a therapeutically effective amount of a compound or composition as disclosed above. The cancer may be breast cancer, such as drug-resistant breast cancer, or prostate cancer, such as castration-resistant prostate cancer.

In another aspect, there is provided a method of reducing expression of one or more stem cell biomarkers in a cancer patient in need thereof comprising administering to the patient a therapeutically effective amount of a compound or composition as disclosed above. The cancer may be as breast cancer, such as drug-resistant breast cancer or triple-negative breast cancer, or prostate cancer, such as castration-resistant prostate cancer.

In another aspect, there is provided a method of reducing metastasis in a cancer patient in need thereof comprising administering to the patient a therapeutically effective amount of a compound or composition as disclosed above. The cancer may be as breast cancer, such as drug-resistant breast cancer, or prostate cancer, such as castration-resistant prostate cancer.

In yet another aspect, there is provided a antibody-drug conjugate comprising:

$$A-L-(X)_y \quad (III)$$

wherein:
  A is an antibody;
  L is a covalent bond or a difunctional linker;
  X is a compound according to claim 1;
  y is an integer selected from 1, 2, 3, 4, 5, 6, 7, 8, 9, 10, 11, 12, 13, 14, 15, 16, 17, 18, 19, or 20.

In still yet another aspect, the present disclosure provides pharmaceutical compositions comprising a compound described herein and an excipient. In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

It is contemplated that any method or composition described herein can be implemented with respect to any other method or composition described herein. For example, a compound synthesized by one method may be used in the preparation of a final compound according to a different method.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1. Chemical structure of MC-1-F2. MC-C is a control compound.

FIGS. 2A-B. Binding validation of MC-1-F2 to FOXC2. FIG. 2A) ELISA-like binding assay to determine binding affinity (Kd) of biotinylated MC-1-F2 (Biotin-MC-1-F2) and biotinylated MC-C (Biotin-MC-C) to full-length FOXC2 or DNA binding domain of FOXC2 (DBD-FOXC2). Triplicate data were fitted in GraphPad Prism. FIG. 2B) DARTS analysis to determine protein stability of FOXC2 and β-actin of cell lysate treated with DMSO (D), 20 μM of MC-C (C) or 20 μM of MC-1-F2 (F2) after pronase treatment for proteolytic degradation. Error bars represent s.d. from triplicate experiments. Statistical comparisons performed by Student's t-test. *p<0.0005; ns=non-significant FIGS. 3A-C. Effect of MC-1-F2 on cell viability and colony forming activity of cell lines with various FOXC2 expression levels. FIG. 3A) MTT cell viability assay of cancer cell lines treated with indicated concentration of MC-1-F2. FIGS. 3B&C) Soft-agar colony formation assay of MCF-7 cells (FIG. 3B) and MDA-MB-231 cells (FIG. 3C) after treatment with DMSO (D), 20 μM of MC-C (C) or 20 μM of MC-1-F2 (F2). Error bars represent s.d. from triplicate experiments. Statistical comparisons performed by Student's t-test. *p<0.0005.

FIGS. 4A-D. Effect of MC-1-F2 on FOXC2 stability and nuclear localization. FIG. 4A) Western blot analysis of FOXC2 in MDA-MB-231 treated with DMSO (D), MC-1-

F2 (F2, 20 μM) or MC-C (C, 20 μM) for 24 hours in the absence or presence MG132. FIGS. 4B&C) Western blot analysis of the cytosolic and nuclear fractions of FOXC2 in MDA-MB-231 treated with DMSO (D), MC-1-F2 (F2, 20 μM) or MC-C (C, 20 μM) for 48 hours. Representative Western blot image (FIG. 4B). β-actin: cytosolic fraction marker. PARP and cleaved PARP: nuclear fraction marker. Quantitative analysis (FIG. 4C). FIG. 4D) Western blot analysis of PDGFR-β expression levels in MDA-MB-231 cells treated with DMSO (D), MC-1-F2 (F2, 20 μM) or MC-C (C, 20 μM) at 24 or 48 hours. Error bars represent s.d. from triplicate experiments. Statistical comparisons performed by Student's t-test. *p<0.0005; p<0.005.

FIGS. 5A-D. Inhibition of EMT and CSC activity by MC-1-F2. Western blot analysis of EMT markers (FIG. 5A), ZEB1 (FIG. 5B), CSC markers (FIG. 5C), and the cytosolic and nuclear fractions of β-catenin (FIG. 5D) of MDA-MB-231 cells treated with 20 μM of DMSO (D) or MC-1-F2 (F2) for 48 hours. Error bars represent s.d. from triplicate experiments. Statistical comparisons performed by Student's t-test. *p<0.0005; p<0.005. See FIGS. 19A&B and 20 for representative Western blot image for FIGS. 5A-C, respectively.

FIGS. 6A-C. Effect of MC-1-F2 on metastatic capabilities of cancer cells. FIG. 6A) Wound-healing assay of MDA-MB-231 cells to measure wound closure over a period of 24 hours after treatment with DMSO (D) or MC-1-F2 (F2, 20 μM). FIG. 6B) Representative image of transwell invasion assay of MDA-MB-231 cells after treatment with DMSO (D) or MC-1-F2 (F2, 20 μM) for 24 hours. FIG. 6C) Quantitation of the invasion assay result. Error bars represent s.d. from triplicate experiments. Statistical comparisons performed by Student's t-test. ***p<0.0005.

FIGS. 7A-B. FIG. 7A) Chemical structure of bi-layered one-bead-one compound triazine-piperazine-triazine library utilized for screening. Inner layer is the peptoid coding sequence and outer layer is actual compound responsible for binding. Theoretical diversity of the library is 87,480 compounds. FIG. 7B) Chemical structures of building blocks used for library synthesis. The structures in brackets are amines used for coding peptoid synthesis when building blocks are not identical.

FIG. 13. Western blot analysis of basal expression levels of FOXC2 of cancer cell lines.

FIG. 14. Western blot analysis of total Bad, phospho-Bad, Bak and Bax of MDA-MB-231 cells treated with DMSO (D) or MC-1-F2 (F2, 20 μM) for 48 hours. **p<0.005

FIGS. 15A&B. Western blot analysis of Snail of MDA-MB-231 cells treated with DMSO (D), MC-C (C, 20 μM) or MC-1-F2 (F2, 20 μM) for 48 hours. FIG. 15A) Representative Western blot image. FIG. 15B) Statistical analysis of the triplicate experiments. ns=non-significant.

FIGS. 16A&B. Western blot analysis of MMP2 of MDA-MB-231 cells treated with DMSO (D), MC-C (C, 20 μM) or MC-1-F2 (F2, 20 μM) for 48 hours. FIG. 16A) Representative Western blot image. FIG. 16B) Statistical analysis of the triplicate experiments. ***p<0.0005.

FIGS. 17A&B. Western blot analysis of p38 of MDA-MB-231 cells treated with DMSO (D), MC-C (C, 20 μM) or MC-1-F2 (F2, 20 μM) for 48 hours. FIG. 17A) Representative Western blot image. FIG. 17B) Statistical analysis of the triplicate experiments. ns=non-significant.

FIGS. 18A&B. Western blot analysis of GSK3β of MDA-MB-231 cells treated with DMSO (D), MC-C (C, 20 μM) or MC-1-F2 (F2, 20 μM) for 48 hours. FIG. 18A) Representative Western blot image. FIG. 18B) Statistical analysis of the triplicate experiments. ns=non-significant.

FIGS. 19A&B. Representative Western blot images of EMT markers (FIG. 19A) and ZEB1 (FIG. 19B) of MDA-MB-231 cells treated with DMSO (D), MC-C (C, 20 μM) or MC-1-F2 (F2, 20 μM) for 48 hours.

FIG. 20. Representative Western blot images of CSC markers of MDA-MB-231 cells treated with DMSO (D), MC-C (C, 20 μM) or MC-1-F2 (F2, 20 μM) for 48 hours.

FIG. 21. Representative wound healing images of MDA-MB-231 cells treated with MC-C (20 μM) at the indicated times after the wound was generated.

FIG. 22. Transwell Invasion assay images of MDA-MB-231 cells treated with DMSO (D), MC-C (C, 20 μM) or MC-1-F2 (F2, 20 μM) for 24 hours.

FIGS. 24A-D. MALDI-TOF and analytical HPLC of MC-1-F2 (FIG. 24A), MC-C (FIG. 24B), biotinylated MC-1-F2 (FIG. 24C), and biotinylated MC-C (FIG. 24D).

FIG. 25. Chemical Structure of MC-1-F2 and MC-C2, a control compound utilized during this study.

FIGS. 26A-G. FIGS. 26A-D) Inhibition of EMT in PC3 cells by MC-1-F2. FIGS. 26A&C) Western blot analysis of EMT markers after treatment with 20 μM of MC-1-F2 (F2), DMSO (D) or MC-C2 (C) for 48 hours. FIGS. 26 B&D) representative western blot image of EMT marker analysis. Error bars represent s.d. from triplicate experiments. Statistical comparisons performed by Student's t-test. *p<0.0005, p<0.005, ns=no statistical difference. FIGS. 26E-G) Inhibition of EMT in DU145 cells by MC-1-F2. FIGS. 26F&G) Western blot analysis of EMT markers after treatment with 20 μM of MC-1-F2 (F2), DMSO (D) or MC-C2 (C) for 48 hours (FIG. 26E) representative western blot image of EMT marker analysis. Error bars represent s.d. from triplicate experiments. Statistical comparisons performed by Student's t-test. *p<0.0005, p<0.005, *p<0.05, ns=no statistical difference.

FIGS. 27A-D. Inhibition of CSC by MC-1-F2. FIGS. 27A&C) Western blot analysis of EMT markers after treatment with 20 μM of MC-1-F2 (F2), DMSO (D) or MC-C2 (C) for 48 hours in PC3 (FIG. 27A) and DU145 (FIG. 27C). FIGS. 27B&D) representative western blot image of EMT marker analysis. Error bars represent s.d. from triplicate experiments. Statistical comparisons performed by Student's t-test. *p<0.0005, p<0.005, *p<0.05.

FIGS. 28A&B. Inhibition of invasive capabilities after treatment with MC-1-F2. FIG. 28A) Transwell invasion assay after treatment with MC-1-F2 (F2) or DMSO (D) for 24 hours. FIG. 28B) Analysis of the number of invading cells from invasion assay. Error bars represent s.d. from triplicate experiments. Statistical comparisons performed by Student's t-test. *p<0.0005, p<0.005.

FIGS. 29A&B. Combinatoric drug treatment of docetaxel with MC-1-F2. FIG. 29A) Dose response curves of co-treatment between Docetaxel and MC-1-F2 at different concentrations with constant ration between the two drugs in both PC3 and Du145 (blue=MC-1-F2, Red=Docetaxel, Green=combination), FIG. 29B) Combination index after co-treatment. Data processing performed utilizing CompuSyn (Chou & Martin, 2007; Zhang et al., 2016).

FIGS. 30A&B. FOXC2 expression levels in prostate cancer cell lines. FIG. 30A) representative western blot image of FOXC2 endogenous levels in LNCaP, DU145 and PC3. FIG. 30B) Image J analysis of western blot performed on FOXC2 expression levels relative to LNCaP. Error bars represent s.d. from triplicate experiments. Statistical comparisons performed by Student's t-test. ***$p<0.0005$.

FIGS. 31A&B. Transwell invasion assay representative images for LNCaP and PC3 cell lines after treatment with MC-1-F2 for 24 hours at 20 μM (FIG. 31A). Image J analysis of the number of invading cells (FIG. 31B). Error bars represent s.d. from triplicate experiments. Statistical comparisons performed by Student's t-test. *$p<0.0005$ FIGS. 32A&B. Cell viability assay for determination of $EC_{50}$ in PC3 (FIG. 32A) and DU145 (FIG. 32B**) with increasing doses of MC-1-F2 over 24 hour treatment. $EC_{50}$ is 46.65 μM and 48.14 μM respectively for PC3 and Du145 cell lines. Error bars represent s.d. from triplicate experiments.

FIGS. 33A&B. Cell viability assay co-treatment with MC-1-F2 and docetaxel (FIG. 33A) or enzalutamide (FIG. 33B) for determination of $EC_{50}$ in PC3 and DU145 with constant ratio between drugs over 24 hour treatment. Error bars represent s.d. from triplicate experiments.

FIGS. 34A&B. AR expression levels after MC-1-F2 treatment for 48 hours at 20 μM in PC3 (FIG. 34A) and Du145 (FIG. 34B). Error bars represent s.d. from triplicate experiments.

FIGS. 35A&B. CompuSyn analysis of drug combination between MC-1-F2 and enzalutamide in PC3 (FIG. 35A) and DU145 (FIG. 35B).

DETAILED DESCRIPTION

Figure 8:
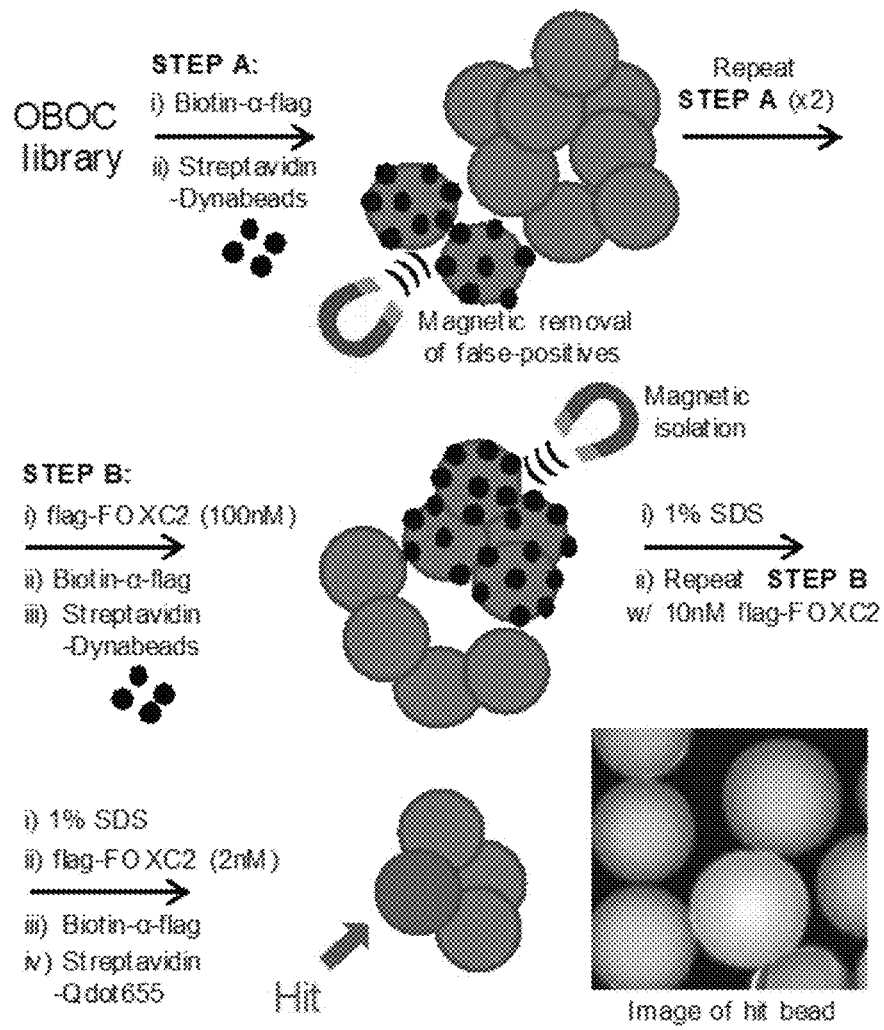
FIG. 8. Screening procedure to isolate small molecule ligand of FOXC2. Fluorescent image was taken with a DAPI filter.

Forkhead box protein C2 (FOXC2; NP_005242), also known as forkhead-related protein FKHL14 (FKHL14), transcription factor FKH-14, or mesenchyme fork head protein 1 (MFH1), is a protein that in humans is encoded by the FOXC2 gene. FOXC2 is a member of the fork head box (FOX) family of transcription factors. The protein is 501 amino acids in length. The gene has no introns; the single exon is approximately 1.5 kb in size.

FOX transcription factors are expressed during development and are associated with a number of cellular and developmental differentiation processes. FOXC2 is required during early development of the kidneys, including differentiation of podocytes and maturation of the glomerular basement membrane. It is also involved in the early development of the heart. An increased expression of FOXC2 in adipocytes can increase the amount of brown adipose tissue leading to lower weight and an increased sensitivity to insulin.

Absence of FOXC2 has been shown to lead to the failure of lymphatic valves to form and problems with lymphatic remodeling. A number of mutations in the FOXC2 gene have been associated with Lymphedema-distichiasis syndrome. It has also been suggested that there may be a link between polymorphisms in FOXC2 and varicose veins.

FOXC2 is also involved in cancer metastases. In particular, expression of FOXC2 is induced when epithelial cells undergo an epithelial-mesenchymal transition (EMT) and become mesenchymal cells. EMT can be induced by a number of genes including Snail, Twist, Goosecoid, and TGF-β1. Overexpression of FOXC2 has been noted in subtypes of breast cancer which are highly metastatic. Suppression of FOXC2 expression using shRNA in a highly metastatic breast cancer model blocks their metastatic ability.

The present disclosure provides a compound and pharmaceutical compositions containing the same. This compound is an antagonist of FOXC2, suppresses EMT and metastasis, and reduces expression of cancer stem cell markers. This compound may be used in antibody drug conjugates, and may be used to treat cancers, such as hormonally-driven cancers like prostate and breast cancers. The compound and methods are described in more detail below.

I. COMPOUNDS AND FORMULATIONS THEREOF

A. Compounds

The compound provided by the present disclosure are shown, for example, above in the summary section and in the examples and claims below. It may be made using the methods outlined in the Examples section. The compound described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The compound described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the (S) or the (R) configuration.

Chemical formulas used to represent the compound described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The compound described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compound described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The compound described herein may also exist in prodrug form. Since prodrugs are known to enhance numerous desirable qualities of pharmaceuticals (e.g., solubility, bioavailability, manufacturing, etc.), the compound employed in methods of the disclosure may, if desired, be delivered in prodrug form. Thus, the disclosure contemplates prodrugs of compounds of the present disclosure as well as methods of delivering prodrugs. Prodrugs of the compound described herein may be prepared by modifying functional groups present in the compound in such a way that the modifications are cleaved, either in routine manipulation or in vivo, to the parent compound. Accordingly, prodrugs include, for example, compound described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compound described herein are within the scope of the disclosure. It will also be appreciated by those skilled in organic chemistry that many organic compounds can exist in more than one crystalline form. For example, crystalline form may vary from solvate to solvate. Thus, all crystalline forms of the compound described herein are within the scope of the present disclosure.

B. Formulations

In some embodiments of the present disclosure, the compound is included in a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the tubulysin analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropyl cellulose, carboxymethyl cellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. CANCER AND OTHER HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the compound described herein may be used to lead to decreased cell counts and as such can potentially be used to treat a variety of types of cancer lines. In some aspects, it is anticipated that the compound described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma;

granular cell carcinoma, follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma, sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma, hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma, astroblastoma, glioblastoma; oligodendroglioma, oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda, et al., 2004). Another example is the cell targeting agents described in U.S. Patent Publication No. 2004/005647 and in Winthrop, el al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay, et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fnl4 receptor, such as TWEAK (see, e.g., Winkles, 2008, Zhou, et al., 2011 and Burkly, el al., 2007, incorporated herein by reference).

A skilled artisan recognizes that there are a variety of known cytokines, including hematopoietins (four-helix bundles) [such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)]; interferons [such as IFN-γ, IFN-α, and IFN-β); immunoglobin superfamily (such as B7.1 (CD80), and B7.2 (B70, CD86)]; TNF family [such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)]; and those unassigned to a particular family [such as TGF-β, IL-1α, IL-β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)]. Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compound of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the tubulysin analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate regulatory agencies for the safety of pharmaceutical agents.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the tubulysin analogs used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the tubulysin analogs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the tubulysin analogs described herein may be used in combination therapies with one or more cancer therapies or a compound which mitigates one or more of the side effects experienced by the patient. It is common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the tubulysin analogs described herein may precede or follow the other treatment by intervals ranging from minutes to weeks. One would generally ensure that a significant period of time did not expire between the times of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1$ and calicheamicin $\omega_1$; dynemicin, including dynemicin A; uncialamycin and derivatives thereof; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, or zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate, an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju el al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides, et al., 1998), cytokine therapy, e.g., interferons α, β, and γ; IL-1, GM-CSF and TNF (Bukowski, et al., 1998; Davidson, et al., 1998; Hellstrand, et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras, et al., 1998; Hanibuchi, et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton, et al., 1992; Mitchell, et al., 1990; Mitchell, et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg, et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

5. Other Agents

It is contemplated that other agents may be used with the compound of the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-β, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 41.1° C.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the appropriate pharmaceutical agent regulatory agencies.

It also should be pointed out that any of the foregoing therapies may prove useful by themselves in treating cancer.

V. SYNTHETIC METHODS

In some aspects, the compound of this disclosure can be synthesized using the methods of organic chemistry as described in this application. These methods can be further modified and optimized using the principles and techniques of organic chemistry as applied by a person skilled in the art.

Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the tubulysin analogs described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H), "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, the formula

covers, for example

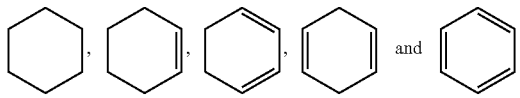

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "〰", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "◁" means a single bond where the group attached to the thick end of the wedge is "into the page". The symbol "〰" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

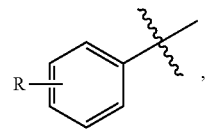

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

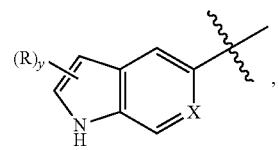

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C\leq 8)}$", "alkynyl$_{(C\leq 8)}$", and "heterocycloalkyl$_{(C\leq 8)}$" is two, the minimum number of carbon atoms in the group "cycloalkyl$_{(C\leq 8)}$" is three, and the minimum number of carbon atoms in the groups "aryl$_{(C\leq 8)}$," and "arenediyl$_{(C\leq 8)}$" is six. "Cn-n'" defines both the minimum (n) and maximum ('n) of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

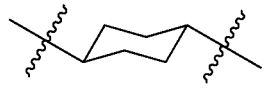 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

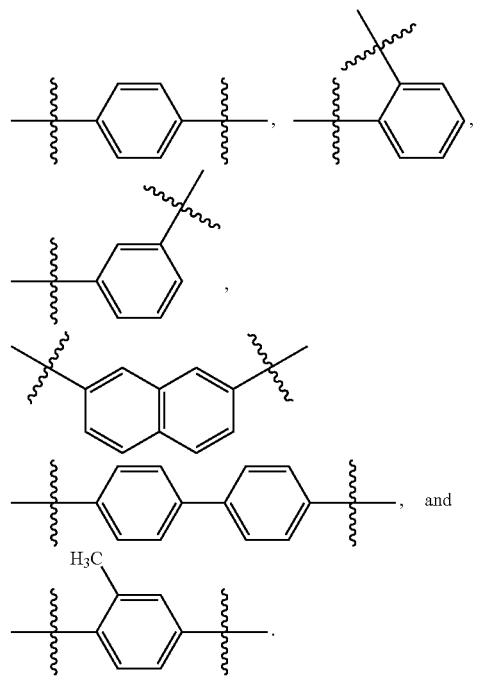

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)CH$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. When any of these terms is used with the "substituted" modifier, one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —NHC(O)OCH₃ and —NHC(O)NHCH₃ are non-limiting examples of substituted amido groups.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies [e.g., shark single domain antibodies (e.g., IgNAR or fragments thereof)], multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')2, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via a nitrogen atom.

A "linker" in the context of this application is divalent chemical group which may be used to join one or more molecules to the compound of the instant disclosure. Linkers may also be an amino acid chain wherein the carboxy and amino terminus serve as the points of attachment for the linker. In some embodiments, the linker contains a reactive functional group, such as a carboxyl, an amide, an amine, a hydroxy, a mercapto, an aldehyde, or a ketone on each end that be used to join one or more molecules to the compounds of the instant disclosure. In some non-limiting examples, —CH₂CH₂CH₂CH₂—, —C(O)CH₂CH₂CH₂—, —OCH₂CH₂NH—, —NHCH₂CH₂NH—, and —(OCH₂CH₂)ₙ—, wherein n is between 1-1000, are linkers.

An "amine protecting group" or "amino protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyl oxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH-$ or $PG_{DA}N-$ wherein $PG_{MA}$ is a monovalent amine protecting group, which may also be described as a "monvalently protected amino group" and $PG_{DA}$ is a divalent amine protecting group as described above, which may also be described as a "divalently protected amino group".

A "hydroxyl protecting group" or "hydroxy protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO$— wherein $PG_H$ is a hydroxyl protecting group as described above.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected thiol group is a group of the formula $PG_TS$— wherein $PG_T$ is a thiol protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedrally substituted carbon centers), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its (R) form, (S) form, or as a mixture of the (R) and (S) forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—a Forkhead Box Protein C2 Inhibitor: Targeting Epithelial-Mesenchymal Transition and Cancer Metastasis The epithelial-mesenchymal transition (EMT) has been suggested as a new target for therapeutic intervention of metastatic cancer. A forkhead Box Protein C2 (FOXC2) is known to be necessary to initiate and maintain EMT, and therefore bestow on cancer cells metastatic and cancer stem cell (CSC)-like phenotypes, allowing cells to acquire higher motility, invasiveness, self-renewal, and therapy-resistance. Here, the first inhibitor of FOXC2-MC-1-F2- is described. MC-1-F2 was able to induce cadherin switching and reverse EMT through the degradation of FOXC2 and blocking its nuclear localization. In addition, MC-1-F2 was very effective in inhibiting cancer cell migration and invasion. As the first small molecule inhibitor of FOXC2 and the first compound targeting EMT-associated transcription factor, MC-1-F2 will pave the way for a new anticancer therapeutic agent targeting metastatic cancer and help to elucidate the network of EMT signaling pathways.

Patients diagnosed with aggressive forms of breast cancer will face the possibility of metastasis and low survival rates (Lin et al., 2013; Dent et al., 2007). The epithelial-mesenchymal transition (EMT) has been thought to be at the forefront of cancer metastasis, identified as a key event in cancer invasion (Singh et al., 2010; Tsai et al., 2013). EMT is a process in which epithelial cells undergo a transition that causes cells to become mesenchymal (Kalluri & Weinberg, 2009; Lee et al., 2006). At the basis of EMT lies the dissolution of cell polarity and cell junctions (Lamouille et al., 2014). This loss of cell junctions leads to the loss of E-cadherin and acquisition of N-cadherin, a hallmark of EMT (Lamouille et al., 2014). EMT is known to be regulated by EMT-associated transcription factors, Snail, Slug, Twist, Goosecoid, ZEB1, and FOXC2. It has also been shown that EMT progression leads to the acquisition of cancer stem cell (CSC) properties (Singh et al., 2010; Mitra et al., 2015). CSC is a small subpopulation of cells in tumors that express traits similar to those of stem cells, primarily the ability to self-renew and generate a heterogeneity of cells (Sato et al., 2016). CSC displays a higher tumor initiating ability as well as chemoresistance and ability to evade immunosurveillance (Mitra et al., 2015; Sato et al., 2016). It is these CSC-like traits that give metastatic cells a more aggressive and recurrent phenotype.

The transcription factor forkhead box protein C2 (FOXC2) belongs to the forkhead family of transcription factors, whose members are involved in various developmental pathways (Fang et al., 2000). Recent studies suggest high levels of FOXC2 are correlated with lymph node metastasis, higher tumor grade and lower overall survival rates (Wang et al., 2014; Li et al., 2015; Lim et al., 2015). It has also been shown that FOXC2 is required for the initiation and maintenance of EMT, as well as acquisition of CSCs traits (Hollier et al., 2013). Several methods for the indirect inhibition of FOXC2 has been explored; the inhibition of a FOXC2 signaling pathways through repression of oncogenic miRNA-520h expression, inhibition of p38 phosphorylation, and inhibition of a down-stream target of FOXC2, PDGFR-β (Hollier et al., 2013; Yu et al., 2013; Werden et al., 2016). These studies have shown that FOXC2 inhibition reverses the effects of EMT, as well as is able to attenuate cancer metastasis, proving a valuable drug target. However, no small molecule inhibitor of FOXC2 has been developed yet. Here, the present disclosure provides the first small molecule inhibitor of FOXC2, MC-1-F2, which modulates EMT progression and cancer metastasis in vitro.

Transcription factors have notoriously been hard to target due to the challenge of inhibiting protein-protein interactions (Moon & Lim et al., 2015). It is known that FOXC2 contains an α-helix domain necessary for its protein-protein interaction and transcriptional activity (Fang et al., 2000). In order to potentially target this domain, we utilized a bi-layered one-bead-one-compound (OBOC) library of α-helix mimetic compounds (FIGS. 7A-B) was used to isolate ligands that bind to full-length FOXC2. This α-helix mimetic library is composed of an outer triazine-piperazine-triazine (TPT) scaffold with substituent groups mimicking the i, i+4 and i+7 side chains of an α-helix (Oh et al., 2014). The inner peptoid of the bi-layered bead serves as the coding sequence for the outer TPT compounds, allowing sequence determination through mass spectrometry.

Figure 9:
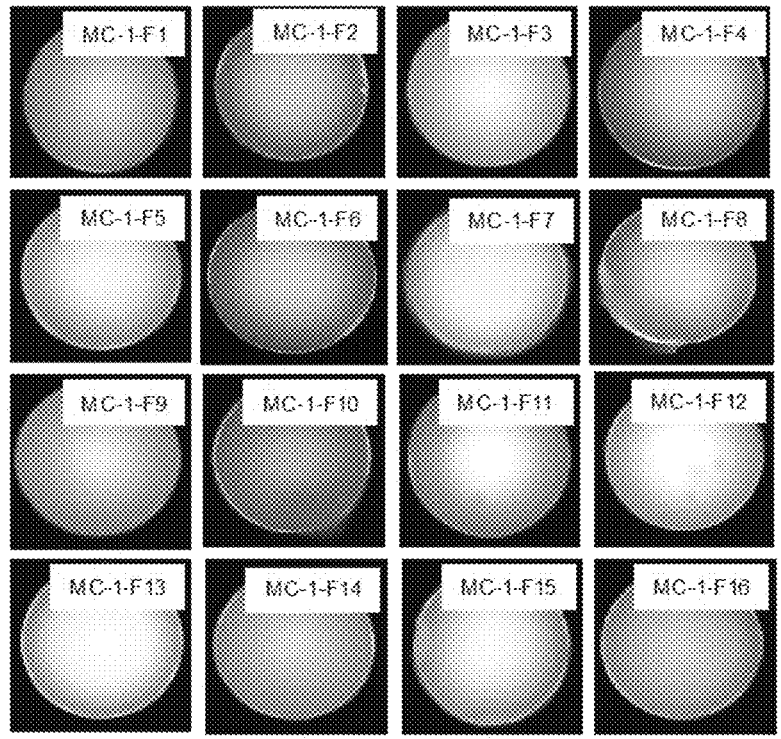
FIG. 9. Fluorescent images of the isolated initial hit beads under DAPI filter.

A screening was carried out utilizing 50 mg of the TPT library beads (~20,400 beads). False-positive binders were first eliminated through incubation of the beads with biotinylated anti-flag antibody and streptavidin-Dynabeads, followed by magnetic removal (FIG. 8). This step (STEP A) was repeated twice to completely remove false-positive binders. Next, the remaining beads were incubated with 100 nM of flag-tagged full-length FOXC2 (flag-FOXC2) followed by biotinylated anti-flag antibody and streptavidin-Dynabeads. The magnetized hit beads were isolated and boiled in 1% SDS to remove any binding protein and Dynabeads (STEP B). In order to select high affinity hits of FOXC2, STEP B was repeated on the isolated beads with decreased concentration (10 nM) of flag-FOXC2. In a final step, 2 nM of flag-FOXC2 incubation followed by biotinylated anti-flag antibody and streptavidin-conjugated Qdot655 were performed to isolate the 16 initial hits (FIG. 9).

Figure 10:
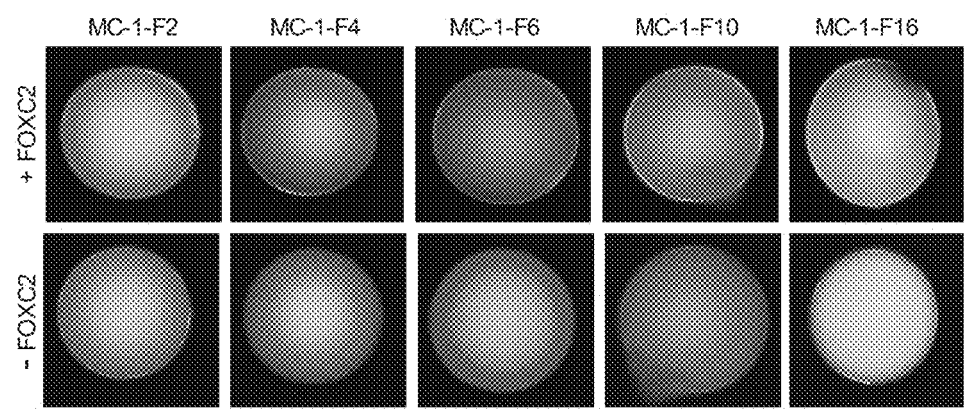
FIG. 10. Fluorescent images of 5 selected hit beads during on-bead validation experiment.
Figure 11:
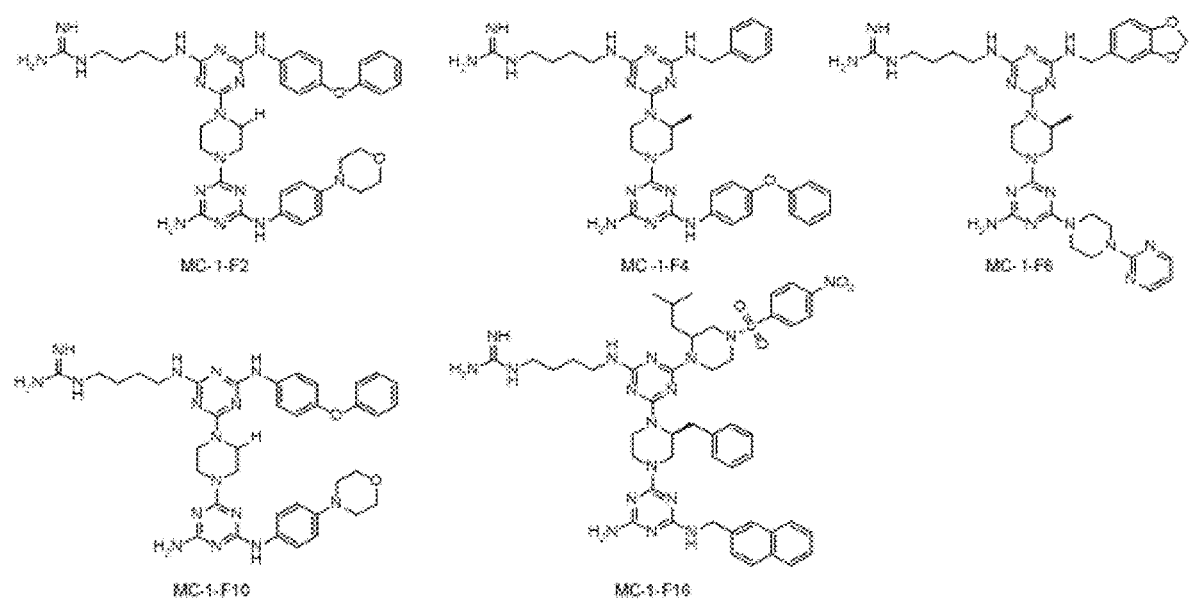
FIG. 11. Chemical structures of hits.

The highly stringent conditions of the screening procedure were expected to yield the complete removal of false-positive binders and result in high-affinity hit ligands. However, in order to further ensure the elimination of false positives, on-bead binding validation was carried out. The 16 hit beads were boiled in 1% SDS to remove any binding protein and incubated with or without flag-FOXC2 and biotinylated anti-flag antibody followed by streptavidin-conjugated Qdot655. The on-bead validation provided 5 hits (FIG. 10) which showed high red fluorescence only in the presence of flag-FOXC2. The five hits (FIGS. 1 and 11) were found to contain an identical guanidine side chain at the upper triazine structure. Moreover, MC-1-F2 and MC-1-F10 were identical (FIG. 11), which gave a strong indication that MC-1-F2 is a true ligand of FOXC2. Therefore, MC-1-F2 was chosen for further characterization of its FOXC2 binding and biological activity.

Figure 12:
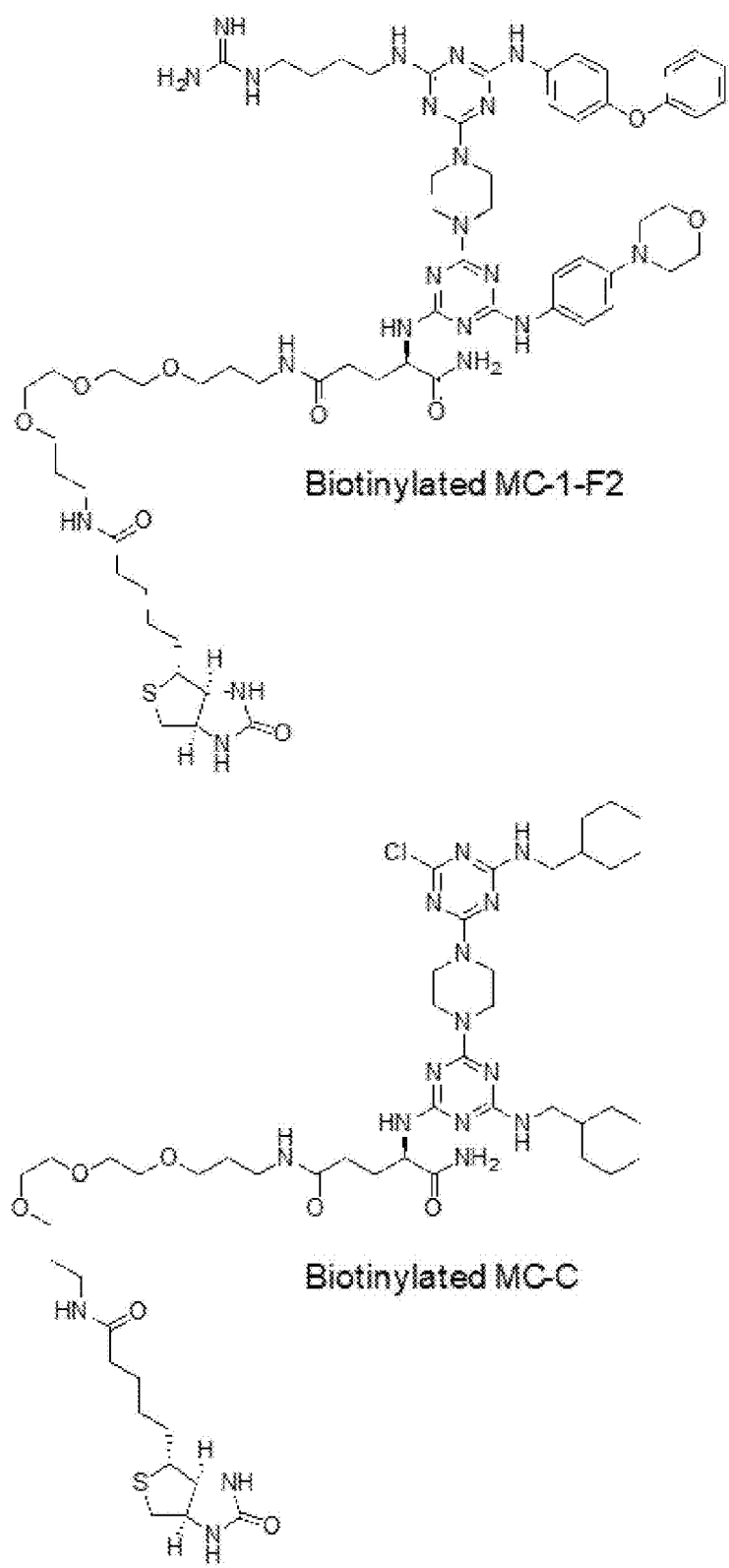
FIG. 12. Chemical structures of biotinylated compounds.
Figure 21:
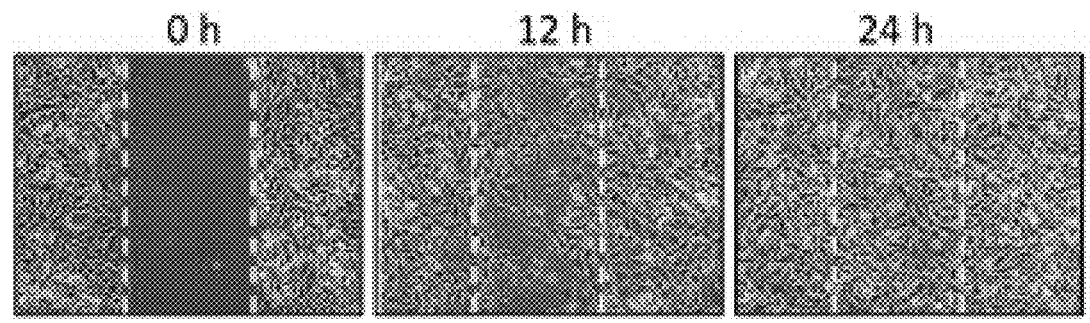
As shown in FIGS. 21, MC-C did not inhibit wound healing.
Figure 22:
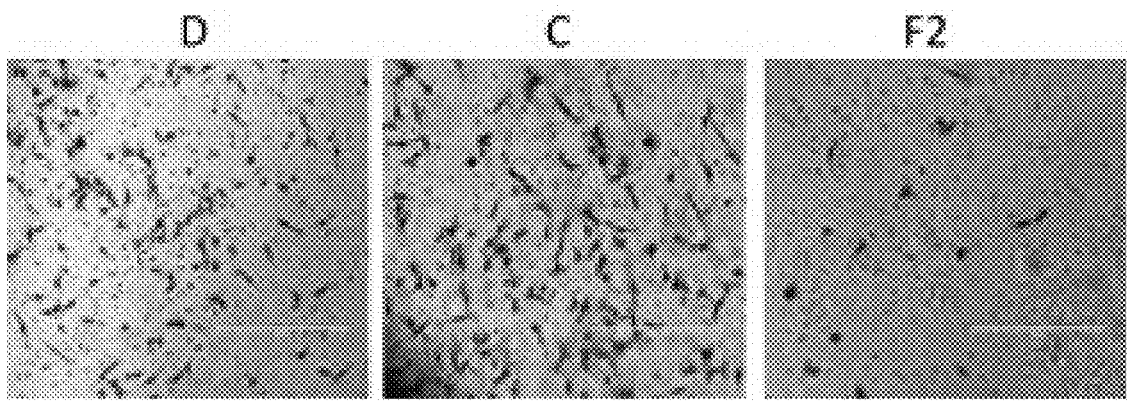
As shown in FIG. 22, MC-C did not inhibit invasion.
Figure 23A:
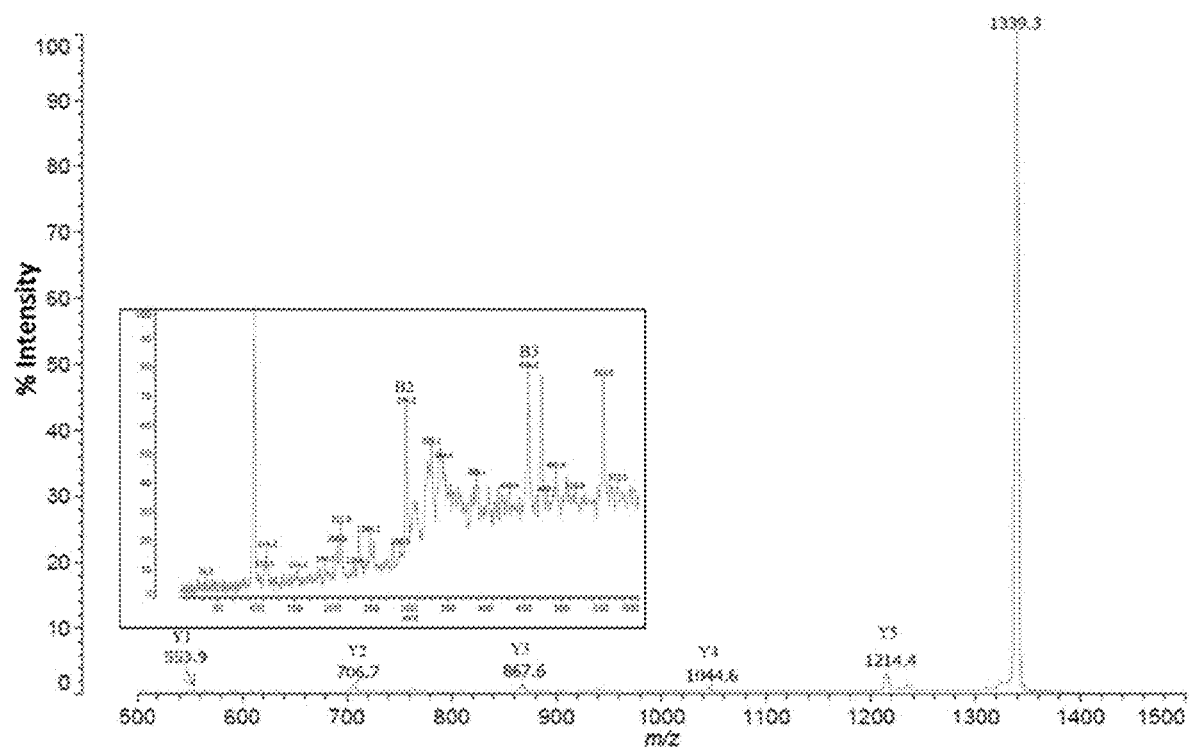
FIGS. 23A-E. Determination of hit structure by sequencing the peptoid coding MC-1-F2 (FIG. 23A), MC-1-F4 (FIG. 23B), MC-1-F6 (FIG. 23C), MC-1-F10 (FIG. 23D), and MC-1-F16 (FIG. 23E).
Figure 23B:
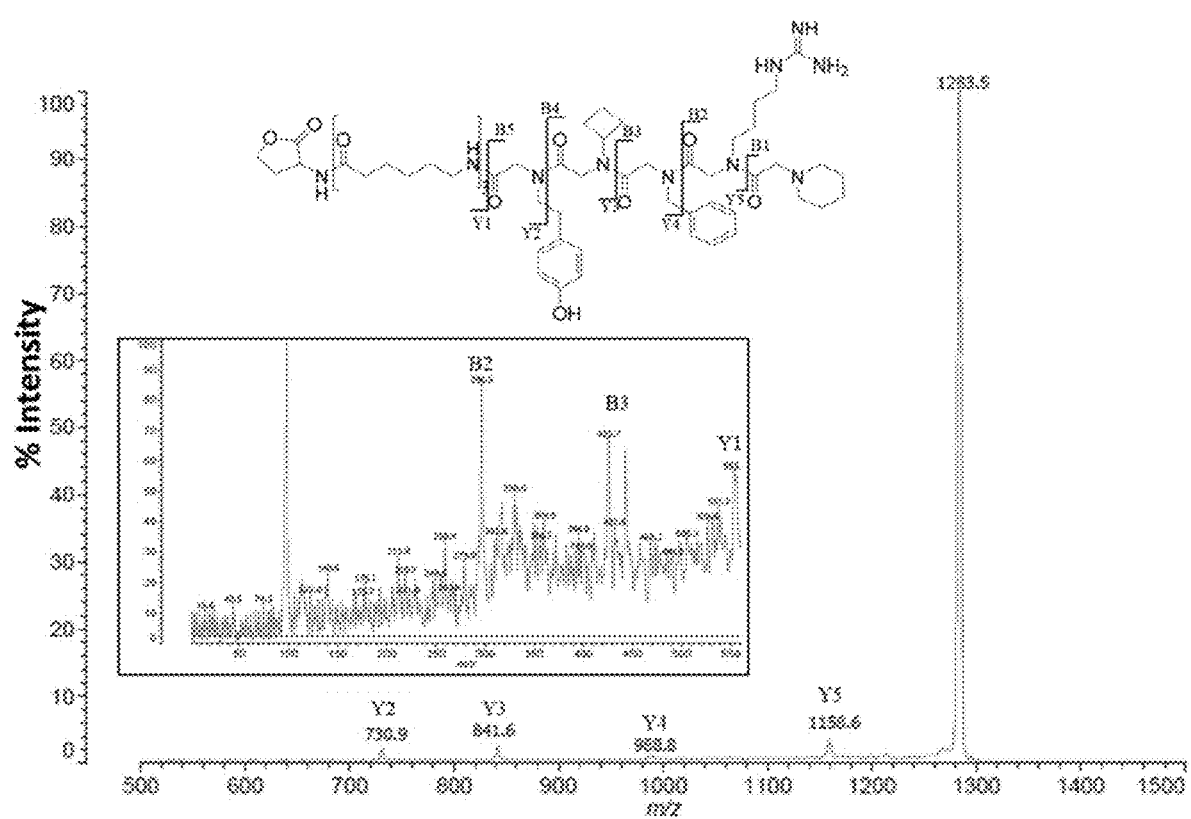
Figure 23C:
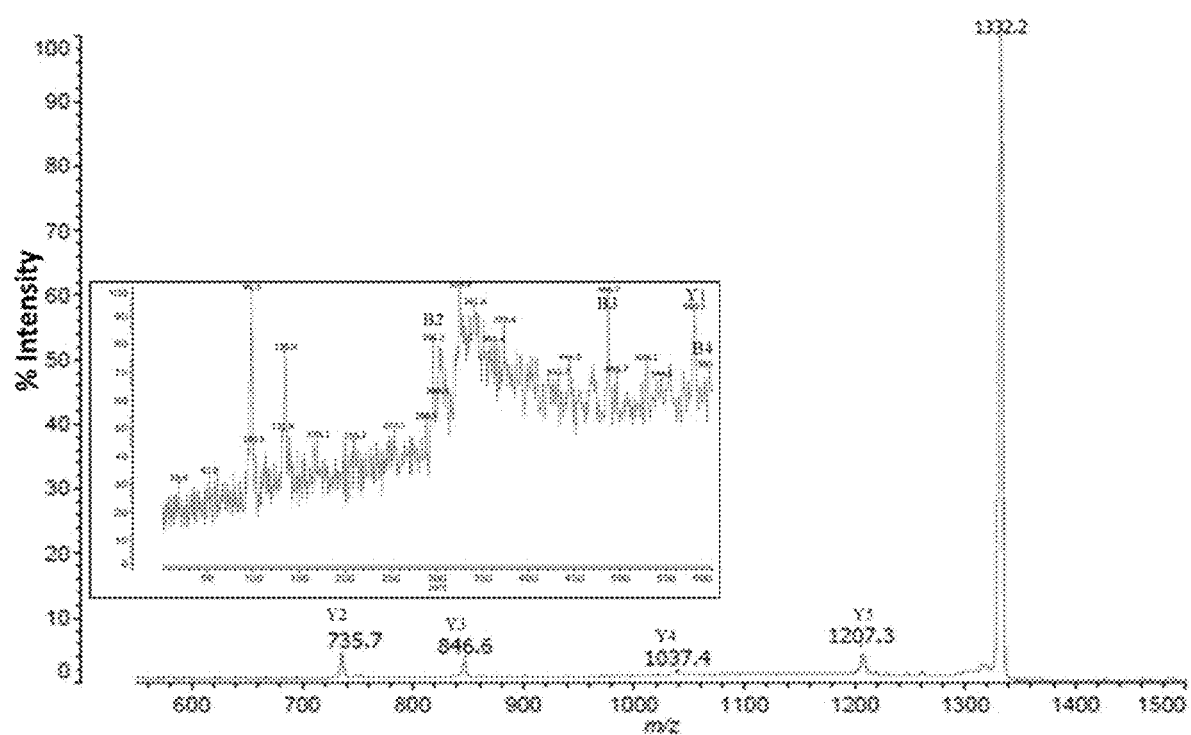
Figure 23D:
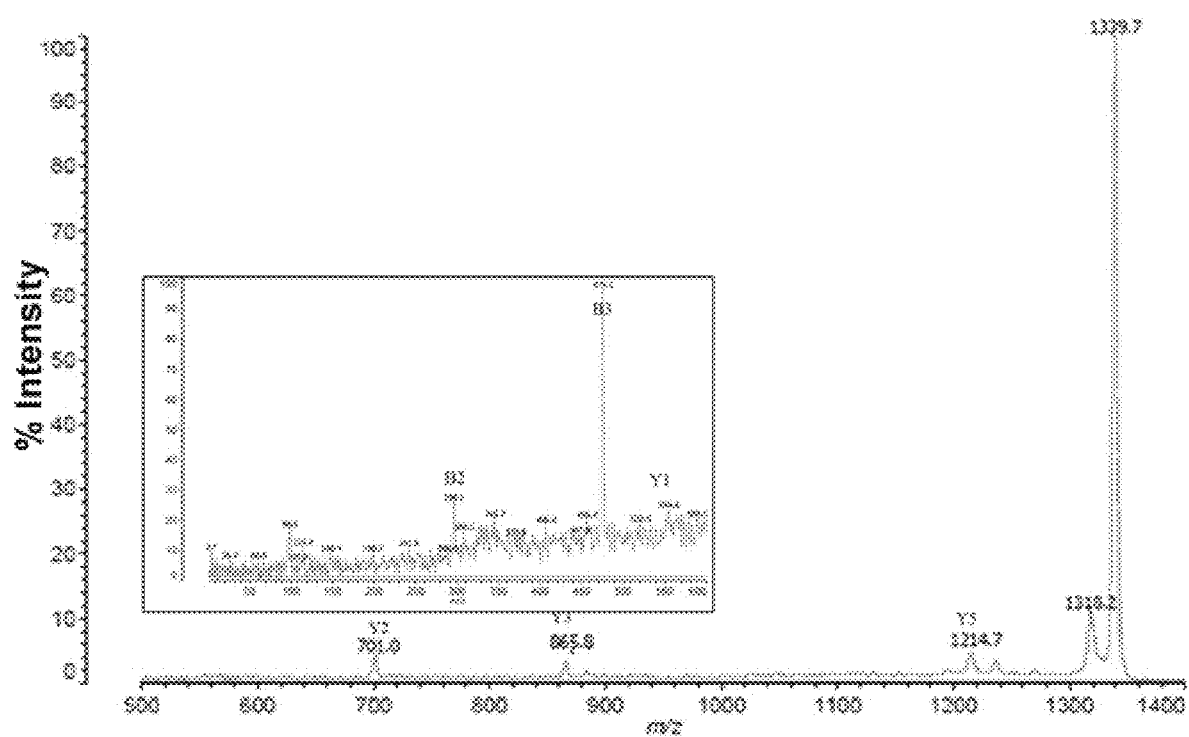
Figure 23E:
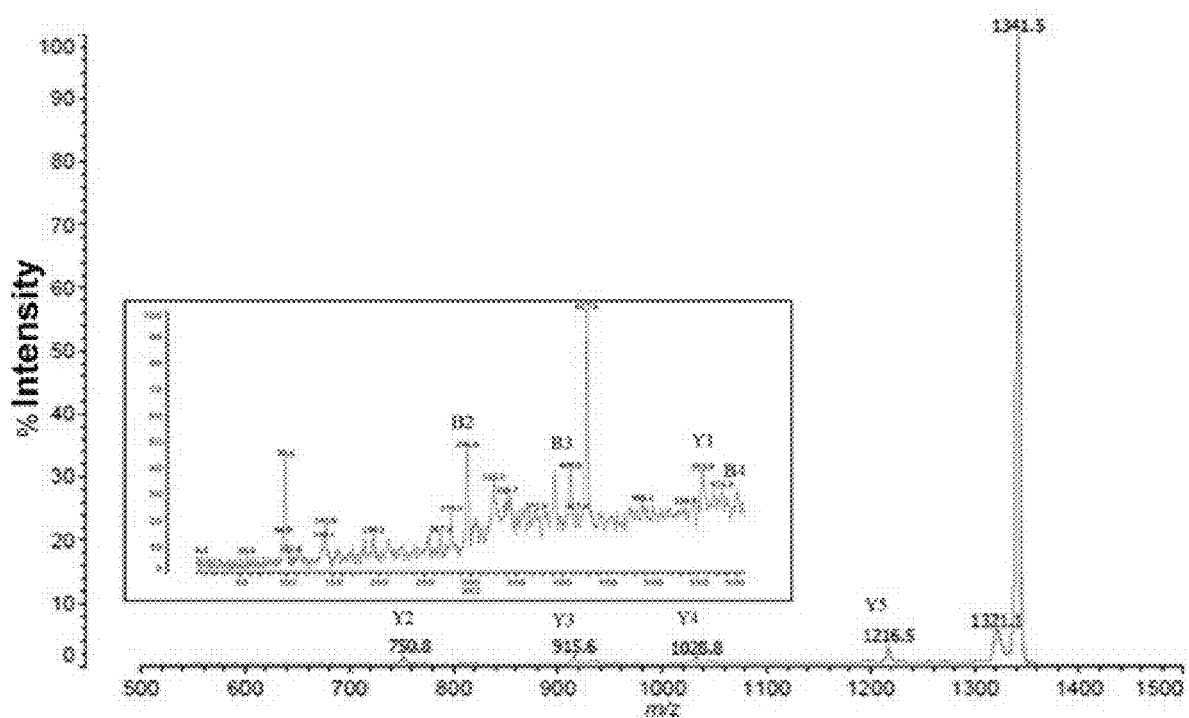

The binding affinity of MC-1-F2 to full-length FOXC2 was determined using an ELISA-like binding assay. In this assay, varying concentrations of biotinylated MC-1-F2 or biotinylated MC-C (control; FIG. 12) were incubated in the wells with immobilized recombinant full-length FOXC2 or the DNA binding domain (DBD) of FOXC2 (FIG. 2A). After washing off unbound ligand, the wells were incubated with streptavidin-conjugated Qdot655, followed by fluorescence measurement of the wells using a plate reader. A $K_d$ of 26 µM was determined for MC-1-F2 binding to the full-length FOXC2. In contrast, MC-C failed to show any binding to FOXC2, indicating the binding of MC-1-F2 to FOXC2 is mediated by the side chains of the MC-1-F2, not by just the TPT scaffold. Moreover, the binding of MC-1-F2 to the DBD-FOXC2 was very weak ($K_d$>100 µM) indicating that the DBD of FOXC2 is not enough for MC-1-F2's binding to FOXC2, and other domains of FOXC2 are involved in binding with MC-1-F2. This is important for the specificity of MC-1-F2 to FOXC2 as several forkhead transcription factors share a very similar DNA-binding domain.

As recombinant FOXC2 was used for the screening and the binding affinity determination, it was important to examine if MC-1-F2 binds to endogenously expressed FOXC2. To this end, a drug affinity responsive target stability assay (DARTS) was performed for MC-1-F2 and MC-C with cell lysate of MDA-MB-231 cells (FIG. 2B). In DARTS, the binding of a small molecule to its cellular target increases protease resistance of the target protein (Pai et al., 2015). The Western blot analysis of the cell lysate incubated with MC-1-F2 showed protection of FOXC2 from pronase-mediated proteolysis, while no FOXC2 protection was observed when the cell lysate was incubated with MC-C. Moreover, MC-1-F2 did not affect the proteolysis β-actin, indicating the protection of FOXC2 proteolysis by MC-1-F2 was due to its specific binding to FOXC2. Collectively, these results have provided strong evidence that MC-1-F2 binds specifically to FOXC2, making it the first synthetic ligand of FOXC2.

It was hypothesized that the specific binding of MC-1-F2 can lead to its specific cellular activity against cancer cells with high FOXC2 expression. This hypothesis was tested by evaluating MC-1-F2's cellular activity on cell lines with different FOXC2 expression levels: MCF-7, BT549, and MDA-MB-231. Both BT549 and MDA-MB-231 cell lines were found to express high levels of FOXC2 expression while MCF-7 contained a very low level of FOXC2 expression (FIG. 13). An MTT cell viability assay showed that MC-1-F2 effectively inhibited cell viability of MDA-MB-231 with estimated $EC_{50}$ of 20 µM, with little inhibition of cell viability of MCF-7 (FIG. 3A). The inhibition of cell viability appeared to occur through an induction of an apoptosis (FIG. 14). However, further studies are still underway. The specificity in cellular activity of MC-1-F2 was further evaluated in the form of a soft-agar colony forming assay to determine if MC-1-F2 was able to inhibit in vitro tumorigenicity of cancer cells in a FOXC2 expression-dependent manner. The results showed that MC-1-F2 displayed strong inhibition of colony forming activity of MDA-MB-231 but not of MCF-7 (FIGS. 3B&C). Overall, these results demonstrated that MC-1-F2 can exert it cellular activity against cells with high FOXC2 expression levels. Further testing is underway in various breast cancer cell lines with different FOXC2 expression levels.

As a transcription factor, FOXC2 needs to localize into the nucleus to promote the transcription of target genes. Therefore, a small molecule that blocks nuclear localization of FOXC2 is expected to inhibit EMT. MDA-MB-231 cells treated with MC-1-F2 showed a decrease in FOXC2 protein level, which was prevented by incubating the cells with a 26S proteasome inhibitor, MG132 (FIG. 4A). This result indicates that MC-1-F2 mediates 26S-proteasomal degradation of FOXC2. Importantly, MC-1-F2 did not affect the protein level of the transcription factor Snail (FIGS. 15A&B) that lies at the upstream of FOXC2 (Wang et al., 2018), demonstrating specificity of MC-1-F2-mediated FOXC2 degradation. Also, MC-1-F2-mediated degradation was accompanied with the decrease in nuclear localization of FOXC2 (FIGS. 4B&C). It has been suggested that phosphorylation of FOXC2 is required for its stability and nuclear localization. Putative kinases that phosphorylate FOXC2 have been proposed (Werden et al., 2016; Ivanov et al., 2013; Golden & Cantley, 2014). It is possible that MC-1-F2 disrupts the protein-protein interaction between FOXC2 and its kinase, resulting in the decease of FOXC2 nuclear localization. Investigation into the exact mechanism by which MC-1-F2 inhibits FOXC2 phosphorylation and nuclear localization is underway.

MC-1-F2's effect on FOXC2-mediated transcription was examined by measuring PDGFR-β expression levels, a downstream effector of FOXC2 (Hollier et al., 2013). MDA-MB-231 cells treated with MC-1-F2 showed a decrease in PDGFR-β expression levels (FIG. 4D). Also, MC-1-F2 downregulated the expression of another FOXC2 target gene, MMP2. (FIGS. 16A&B). To validate the specificity of the ligand to FOXC2, Western blot analysis was carried out on the non-target genes of FOXC2, p38 and GSK3P3. The Western blot results showed that MC-1-F2 displayed no effect on the expression levels of P38 and GSK30 (FIGS. 17A&B and 18A&B). Collectively, MC-1-F2 was shown to inhibit the activity of FOXC2 by inducing its degradation and blocking its nuclear localization.

Next, it was examined if FOXC2 inhibition by MC-1-F2 can affect EMT progression. EMT progression is marked by a cadherins in cells, in which E-cadherin is downregulated and N-cadherin is upregulated. It has been shown that inhibition of downstream or upstream targets of other EMT-associated transcription factors such as Snail, Slug and Twist leads to the decreased EMT progression, through the re-expression of E-cadherin (Bachelder et al., 2005; Ren et al., 2013). However, the impact of direct inhibition of EMT-associated transcription factors including FOXC2 on EMT progression has never been explored until now due to the lack of small molecule inhibitors directly targeting these transcription factors. Western blot analysis of EMT markers in MDA-MB-231 cells treated with MC-1-F2 showed a cadherin switching (FIG. 5A). MC-1-F2 is able to increase E-cadherin expression and lead to the downregulation of N-cadherin, along with a decrease in other mesenchymal markers such as Vimentin and Slug (FIG. 5A). These results on EMT markers provides strong evidence that MC-1-F2 is able to reverse EMT progression in vitro.

Another EMT-regulating transcription factor, ZEB1 is a downstream transcription target of FOXC2 and has been shown to modulate E-cadherin expression (Werden et al., 2016; Schmalhofer et al., 2009). Therefore, it was examined if the increase of E-cadherin by MC-1-F2 is due to the suppression of ZEB1. The Western blot result showed that MC-1-F2 was able to downregulate ZEB1 (FIG. 5B). ZEB1 is also associated with the development of chemoresistance of cells that have undergone EMT, and its inhibition was shown to restore drug sensitivity of cancer cells (Zhang et al., 2015). Therefore, MC-1-F2 can not only reverse EMT, but also possibly restore drug sensitivity. Studies are underway to examine MC-1-F2's ability to re-sensitize cancer cells to chemotherapy. It is also important to note that the exact role which FOXC2 plays in terms of activating EMT associated transcription factors was not yet validated. In this study, the inhibition of FOXC2 was correlated with a downregulation of Slug and ZEB1. Further studies with MC-1-F2 will help to elucidate the exact role of FOXC2 in EMT and its regulation of EMT associated transcription factors.

As EMT is known to bestow on cells CSC-like properties (Hollier et al., 2013), MC-1-F2 should be able to repress CSC characteristics in cells undergoing EMT. In order to examine the effects of MC-1-F2 on CSC properties, a Western blot analysis of MDA-MB-231 cell with and without treatment of MC-1-F2 was carried out, analyzing the CSC markers c-Myc, KLF4, and Nanog. The results showed a decrease of c-Myc and KLF4 with no statistical difference in Nanog expression after treatment with 20 µM of MC-1-F2 for 48 hours (FIG. 5C). In order to further evaluate the effect of MC-1-F2 on CSC properties and EMT progression, β-catenin nuclear localization was examined (FIG. 5D). β-catenin is involved in both EMT progression and acquisition of CSC properties (Kalluri & Weinberg, 2009, Schmalhofer et al., 2009). A repression of E-cadherin has shown to initiate a nuclear localization of β-catenin, leading to an initiation of several EMT signals (Schmalhofer et al., 2009). Moreover, nuclear localization β-catenin is the hallmark of an active Wnt pathway, a major pathway that contributes to CSC properties (Beck & Blanpain, 2013). Treatment with 20 µM MC-1-F2 showed a decrease in the nuclear fraction and an increase in the cytosolic fractions of β-catenin. Only nuclear fraction of β-catenin bestows CSC properties on cells. Collectively, these results strongly indicate the ability of MC-1-F2 to inhibit EMT/CSC properties of breast cancer cell in vitro.

Reversal of EMT mediated by MC-1-F2 was anticipated to lead to the inhibition of metastatic capability of cancer cells. Thus, in vitro assays were carried out to demonstrate the ligand's effect on migratory and invasive capabilities of cancer cells. A wound healing assay was carried out to examine the migratory capabilities of cells in closing a "wound" or gap over a period of 24 hours. The assay showed inhibition of the migratory activity of MDA-MB-231 cells treated with MC-1-F2 (FIG. 6A). Inhibition of migratory capabilities of cells only measures one aspect of EMT progression. EMT is marked also by increased invasiveness of cancer cells. Therefore, the invasive property of MDA- MB-231 cells treated with MC-1-F2 was examined (FIGS. 6B&C). The invasion assay demonstrated a decrease in the invasive property of MC-1-F2 treated MDA-MB-231 cells as compared to both the DMSO and MC-C treated cells. These data provide strong evidence that MC-1-F2 inhibits cancer cell metastasis in vitro.

In this study, the first small molecule inhibitor of FOXC2, MC-1-F2, was discovered via a high-throughput screening of a combinatorial α-helix mimetic library. Binding of MC-1-F2 to FOXC2 was confirmed by evaluating its binding to recombinant full-length FOXC2 as well as endogenous FOXC2 in cancer cells. Importantly, MC-1-F2 displayed specific anti-tumor activity such as cytotoxicity and anti-proliferative activity against cancer cell lines in a FOXC2 expression level-dependent manner. Also, the binding of MC-1-F2 to FOXC2 led to the degradation of FOXC2 and the decrease of its nuclear localization. Importantly, FOXC2 inhibition by MC-1-F2 induced cadherin switching; upregulation of E-cadherin and downregulation of N-cadherin, along with a decreased expression of mesenchymal markers such as Vimentin, Slug, and ZEB1. Upregulation of E-cadherin was found to be concurrent with the suppression of the nuclear localization off β-catenin. Moreover, the reversal of EMT was accompanied with a decrease in CSC maker expression. Most importantly, MC-1-F2 was found to inhibit cancer metastasis in vitro.

MC-1-F2 is the first small molecule inhibitor of FOXC2 and the first inhibitor of EMT-associated transcription factor. As such, discovery of MC-1-F2 provides not only a novel anti-cancer therapeutic candidate targeting cancer metastasis but also a very important chemical probe to elucidate mechanisms by which FOXC2 orchestrates the EMT signaling network. Immediate future work is to investigate in vivo effects of MC-1-F2 on primary tumor growth and metastasis. Previous in vivo studies with indirect inhibition of FOXC2 have yielded conflicting results, with one study demonstrating inhibition of both primary tumor growth and metastatic progression (Hollier et al., 2013) while other study demonstrating only inhibition of metastatic progression (Werden et al., 2016). MC-1-F2, as the first small molecule inhibitor of FOXC2, will be able to elucidate whether FOXC2 inhibition has an effect on primary tumor growth as well as the reported inhibition on metastatic progression.

Example 2—Experimental Methods for Example 1

Construction of α-helix mimetic library. The library constructed as reported previously (Oh et al., 2014).

High Throughput Screening Procedure.

50 mg of library was deprotected using TFA solution (95% TFA, 2.5% TIS, 2.5% $H_2O$) for 2 hours. The solution was decanted and the beads were blocked in PBST assay buffer (PBST with 0.10% gelatin and 2% BSA) at 4° C. for 1 hour. The beads were incubated in 5 mL PBST assay buffer and 10 µL of streptavidin-Dynabeads (Invitrogen) for 1 hour at 4° C. Followed by the addition of 10 µL anti-flag biotin (Invitrogen) for 1 hour at 4° C. Magnetized beads (non-specific binders) were removed. Removal of non-specific binders was repeated twice. The solution was decanted and beads were incubated in 100 nM flag-FOXC2 in PBST assay buffer at 4° C. over-night. Followed by 1 hour incubation of anti-flag-biotin and streptavidin-Dynabeads consecutively at 4° C. Magnetized beads were regarded as preliminary hits. Beads were boiled in 1% SDS and a second round of hit isolation was carried out in 10 nM flag-FOXC2. Subsequently, the hit beads were boiled in 1% SDS and incubated with flag-FOXC2 (2 nM), biotinylated anti-flag antibody and strepavidin-Qdot655 (Invitrogen). Beads were visualized under DAPI filter and hit beads were isolated.

On-Bead Validation.

The isolated hit beads were boiled in 1% SDS and incubated in 0.5 mL PBST buffer, 0.25 µL of anti-flag biotin at 4'C for 1 hour. Followed by incubation with 0.25 µL of strepavidin-Qdot655 at 4° C. for 1 hour. The beads were then visualized under DAPI filter. Beads that are specific to FOXC2 showed no fluorescence under these conditions. MALDI-TOF analysis was performed for sequence determination after CNBr reaction of each hit bead.

Synthesis of MC-1-F2.

100 mg of MBHA Rink Amide beads (Novabiochem) were swelled in DMF for 1 hour and followed by deprotection with 20% piperidine. After a full wash (3×DMF, 2×MeOH, 2×DCM, 3×DMF), 4,6-dichloro-N-(4-phenoxyphenyl)-1,3,5-triazin-2-amine (5 eq.) was added in dry NMP followed by DIPEA (10 eq.) and mixed at room temperature for 5 hours. Unless stated, all beads were subject to a full wash after each reaction step. 1-[(4-Nitrophenyl)sulfonyl]piperazine (5 eq.) in dry NMP with DIPEA (10 eq.) was added and reacted at 60° C. overnight. The beads were deprotected using DBU (10 eq.) and 2-mercaptoethanol (10 eq.) for 3 hours at room temperature. Followed was the addition of the 4,6-dichloro-N-[4-(4-morpholinyl)phenyl]-1,3,5-triazin-2-amine (5 eq.) in dry NMP and DIPEA (10 eq.) at 60'C for 5 hours. Followed by the addition of 1-(4-aminobutyl)guanidine (10 eq.) in dry NMP with DIPEA (20 eq.) at 60° C. overnight. The beads were cleaved and deprotected in TFA solution (95% TFA, 2.5% TIS, 2.5% $H_2O$) for 2 hours. The resulting solution was concentrated and purified by column chromatography (DCM with 20% MeOH and 0.1% $NH_4OH$), affording a yellow solid product in 600/% yield. $^1H$ NMR (500 MHz DMSO-$d_6$) δ (major, ppm) 7.68-7.55 (d, 2H), 7.55-7.35 (d, 2H), 7.44-7.30 (m, 2H), 7.12-7.05 (m, 1H), 6.86-6.98 (m, 4H), 6.82-6.89 (d, 2H), 3.72-3.73 (s, 4H), 3.41 (s, 8H), 3.16 (m, 4H), 3.02 (m, 4H), 1.48-1.53 (m, 2H), 1.20-1.23 (m, 2H). MALDI-TOF $[M+H]^+$ 747.9 (calc. 746.9).

Synthesis of MC-C.

100 mg of MBHA Rink Amide beads (Novabiochem) were swelled in DMF for 1 hour and followed by deprotection with 20% piperidine. After a full wash (3×DMF, 2×MeOH, 2×DCM, 3×DMF), 4,6-dichloro-N-(cyclohexylmethyl)-1,3,5-Triazin-2-amine (5 eq.) was added in dry NMP followed by DIPEA (10 eq.) and mixed at room temperature for 5 hours. Unless stated all beads were subject to a full wash after each addition. 1-[(4-Nitrophenyl)sulfonyl]piperazine (5 eq.) in dry NMP with DIPEA (10 eq.) was added and reacted at 60'C overnight. The beads were deprotected using DBU (10 eq.) and 2-mercaptoethanol (10 eq.) for 3 hours at room temperature. Followed was the addition of the 4,6-dichloro-N-(cyclohexylmethyl)-1,3,5-triazin-2-amine (5 eq.) in dry NMP and DIPEA (10 eq.) at 60° C. for 5 hours. The beads were cleaved and deprotected in TFA solution (95% TFA, 2.5% TIS, 2.5% $H_2O$) for 2 hours. The resulting solution was concentrated and purified by column chromatography (DCM with 3% MeOH and 0.1% $NH_4OH$), affording a white solid product in 65% yield. $^1H$ NMR (500 MHz, $CDCl_3$) δ (major, ppm) 3.85-3.83 (m, 8H), 3.26-3.21 (m, 4H), 1.8-1.72 (m, 10H), 1.26-1.23 (m, 10H), 1.0-0.97 (m, 2H). MALDI-TOF $[M+H]^+$ 516.9 (calc. 516.1).

Biotinylated Compound Synthesis.

100 mg of MBHA Rink Amide beads (Novabiochem) were swelled in DMF for 1 hour and followed by deprotection with 20% piperidine. After a full wash (3×DMF, 2×MeOH, 2×DCM, 3×DMF), the beads were incubated with Fmoc-Glu(biotinyl-PEG)-OH (Chem-Impex Int'l. Inc.) (3 eq.), HOBT (Creosalus) (5 eq.), HBTU (AnaSpec) (5 eq.) and DIPEA (10 eq.) in DMF at room temperature for 3 hours. After the beads were treated with 20% piperidine, reaction steps in the synthesis of MC-1-F2 and MC-C were performed to afford biotinylated MC-1-F2 and biotinylated MC-C, respectively. Biotinylated-MC-1-F2: yield 600%, MALDI-TOF $[M+H]^+$ 1305.12 (calc. 1304.6). Biotinylated-MC-C: yield 65%, MALDI-TOF $[M+H]^+$1076.94 (calc. 1073.8).

Cell Lines and Cell Culture.

MCF-7 and MDA-MB-231 were cultured in Hyclone Dulbecco's Modified Eagle Medium (DMEM) with high glucose (4.5 g/L) content. BT549 cells were grown in Hyclone Roswell Park Memorial Institute (RPMI) 1640 medium. All cell culture media were supplemented with 10% bovine growth serum (BGS), 1% L-glutamine and 0.5% Penicillin/Streptomycin antibiotic, and the cultured cells were maintained in a 37° C. incubator with 5% $CO_2$. Cell culture media and supplements were purchased from Fisher Scientific unless otherwise indicated. Cell lines were purchased from American Type Culture Collection (ATTC).

Cloning, Expression, and Purification of FOXC2 Proteins.

The DNA encoding the human FOXC2 protein (amino acid residues 1-501) with a C-terminal 6 histidine tag was cloned between the Nde I and Xho I restriction sites of a modified pET-28a expression vector. The expression vector was modified to include coding sequences for 3 FLAG-tags and Tobacco Etch Virus protease (TEV) recognition motif at the 5' section of the multiple cloning site. The FOXC2 DNA binding domain (DBD, residues 60 to 163) was inserted between Nde I and EcoR I sites of a modified pET 28b plasmid containing N-terminal 6 histidine and maltose binding protein (MBP) tags cleavable using TEV. For protein expression, E. coli BL21(DE3) and BL21 (DE3)-RIPL cells were transformed with the full length FOXC2 and FOXC2 DBD expression constructs, respectively, and grown in Luria Broth. Protein expression was induced with 0.4 mM of β-D-1-thiogalactopyranoside for 4 hours at 37° C.

The FOXC2 full-length protein was purified by a standard affinity chromatography method. First, cells were lysed by sonicating for 4 minutes in 50 mM Tris-HCl pH 8.0, 150 mM NaCl, 20% Glycerol (v/w), 2 mM $MgCl_2$, and 2 mM β-mercaptoethanol (BME). A protease inhibitor cocktail tablet (Roche Life Science) and 0.2% polyethyleneimine were added to the lysed sample. The cell lysate was clarified by centrifugation at 35,000 g for 30 minutes, and applied to HisTrap nickel-affinity column (GE Healthcare). The protein was eluted from the nickel-affinity column with a linear imidazole gradient from 50 mM to 500 mM in 50 mM Tris-HCl pH 8.0, 500 mM NaCl, 10% Glycerol, and 2 mM BME. The peak fractions were pooled and subjected to the second round of affinity chromatography following the same procedure. The purified protein was buffer-exchanged to 50 mM Tris-HCl pH 8.0, 150 mM NaCl, 10% Glycerol (v/w), 2 mM $MgCl_2$ and 2 mM BME, and concentrated using Amicon Ultra MWCO 10,000 (Millipore).

The FOXC2 DBD protein was expressed and the cell lysate was prepared in Lysis Buffer containing 50 mM Tris-HCl pH 7.0, 150 mM NaCl, 20% Glycerol, 2 mM $MgCl_2$, and 2 mM BME following the protocol of the FOXC2 full length protein. Cobalt charged Sepharose beads (GE Healthcare) were used for affinity chromatography purification. The supernatant of the cell lysate was applied to the column, which was washed with Lysis Buffer containing 5 mM imidazole. The protein was eluted with 750 mM imidazole. To remove the bulky fusion tag, the eluted fractions were incubated with TEV during an overnight dialysis step against a buffer composed of 50 mM Tris-HCl pH 7.0, 100 mM NaCl, 12% Glycerol (v/w), 2 mM $MgCl_2$ and 2 mM BME at 4° C. The protein was further purified by cation exchange chromatography using Hi-Trap S column (GE Healthcare). The cleaved proteins were eluted by a linear NaCl gradient from 50 mM to 1 M at pH 7.0. The protein was further purified using Superdex 75 gel filtration column (GE HealthCare) and concentrated using Amicon Ultra MW 3,000 (Millipore). The purified proteins were analyzed by SDS-PAGE throughout the purification steps.

Cell Viability Assay.

Cell viability was assessed by MTT (3-(4,5-Dimethylthiazol-2-yl)-2,5-Diphenyltetrazolium Bromide) assay. $1 \times 10^4$ cells were seeded on 48-well cell culture plate, and were incubated for at least 24 hours prior to drug treatment. The MTT reagent (Fisher Scientific) was added to the culture medium 3 hours prior to the end of compound incubation. The reaction took place in the 37° C. incubator with 5% $CO_2$ for 3 hours. Cell culture medium was then removed from the wells. Cells with the insoluble purple formazan were lysed with DMSO for 10 mins at room temperature, 0.5 ml per well. The solution was aliquot to 96-well plate for absorbance reading at 570 nm using a plate reader.

Wound Healing Assay.

$3 \times 10^5$ cells of MDA-MB-231 in 70 µL of DMEM media were seeded on an ibidi µ-dish (Ibidi) and incubated for 24 hours. The insert was removed carefully with tweezers, to create the "wound" and the dish rinsed with DPBS. Followed by the addition of DMEM media with applicable drug. Images were taken at various time points and monitoring of the migration of cells into the "gap" was recorded at several time points.

Soft-Agar Colony-Forming Assay.

Soft-agar colony-formation assay was performed in 6-well plates. $5 \times 10^3$ cells were re-suspended into 1.5 mL 0.3% agarose-DMEM mixture, and seeded onto the 0.5% agarose-DMEM base layer. FBS-supplemented DMEM medium (0.2 mL) containing the compound of determined concentrations was added on the top and changed every 3 days. After 10 days incubation in 37° C. incubator with 5% $CO_2$, 0.5 mL of 0.005% crystal violet solution was added to the top of the agarose gel and incubated overnight. The total number of colonies per well that were >100 microns in size when viewed under a simple microscope were counted. Light microscopy images were captured under 20× magnification.

SDS-PAGE and Western Blot Analysis.

50 µg of total protein per sample was incubated with 4× loading buffer at 100° C. for 5 min. Protein samples were then loaded into a polyacrylamide gel and subjected to SDS-PAGE. Resolved proteins were then transferred by a wet transfer method to a PVDF membrane at 100 V for 1 hour using a BioRad Mini Trans-Blot Electrophoresis Transfer Cell. Upon the completion of wet transfer, the membrane was then blocked with 5% (w/v) fat-free milk in 1× Tris-buffered saline/0.1% (v/v) Tween-20 (TBS-T) for at least 1 hour. Then incubated with the respective primary antibodies diluted in 5% BSA in 1×TBST at 4° C. overnight. The following day exposed to 1:1000 dilution of anti-mouse or anti-rabbit HRP-conjugated secondary antibodies in 5% (w/v) fat-free milk in 1×TBS-T for 1 hour at room temperature. The probed proteins were then detected for chemiluminescent signal using SuperSignal Chemiluminescent Substrate (PIERCE). Pierce antibodies: B-actin, and all other antibodies used are from cell signaling. MG132 treatment was added to cells (0.5 µM) for 1-hour incubation prior to compound treatment, no more than 24 hours total exceeded during MG132 incubation.

Drug Affinity Responsive Target Stability (DARTS) Assay.

MDA-MB-231 cell lysate was harvested and incubated with 600 µL of Triton X-100 lysis buffer (50 mM Tris-HCl, 150 mM NaCl, 1 mM EDTA, 1% Triton X-100, pH 8.0) with protease inhibitor and 150 µL of phosphate inhibitor was added. Then frozen overnight followed by addition of 66.7 µL of 10×TNC buffer (1 M Tris-HCl, 5 M NaCl, 1 M $CaCl_2$, pH 8.0) and gently mixed. The lysate was further split into 2 test tubes: Tube (1) 300 µL, Tube (2) 300 µL of cell lysate. The samples were incubated in desired concentration of compounds for 1 hour at room temperature and gently mixed. Once done the lysate of each condition was further split into 5 test tubes for each pronase condition. Pronase stock solution was thawed prior to use and 2 µL of each concentration were added to each tube and allowed to incubate for 20-30 minutes, followed by the addition of SDS loading buffer to stop pronase digestion followed by Western blot analysis.

ELISA-Like Binding Assay.

Clear bottom, black wall, 96 well plate (Corning) was coated with 1 µg/mL of full length FOXC2 or DNA binding domain (DBD) of FOXC2 protein in sensitizing buffer (0.621 g $NaHCO_3$, 0.275 g $Na_2CO_3$ in 100 mL of water pH=9.5) overnight at 4° C. Wells were washed 3 times with 200 µL of wash buffer (1x PBS with 0.05% Tween-20). Wells were blocked with blocking buffer (1% BSA in 1×PBS with 0.05% Tween-20) for 1 hour at room temperature. 50 µL of serial dilutions of biotinylated compound in blocking buffer were added to each well and incubated for 1 hour at room temperature. Followed was the addition of 50 L of 20 nM of strepavidin-Qdot655 in blocking buffer for 1 hour at room temperature. Wells were then washed 5 times with wash buffer. Fluorescence was measured using a plate reader (Ex. 495, Em. 655).

Transwell Invasion Assay.

Matrigel invasion chambers (Corning) were allowed to come to room temperature and allowed to rehydrate for 2 hours in a cell incubator. Cells were treated 24 hours prior to assay and starved in 2% FBS in DMEM for 2 hours prior to assay. A cell suspension containing $5 \times 10^4$ cells/mL was prepared. Chemoattractant (DMEM+10% FBS) was added to the bottom of the wells. Using forceps, the inserts were transferred inside the wells and 0.5 mL of cell suspension was immediately added. The chambers were incubated for 22 hours in a humidified tissue culture incubator. After the 22 hours, the non-invading cells were removed by scrubbing the surface of the membrane. The cells were fixated with 4% formaldehyde solution for 2 minutes at room temperature. Followed by permeabilization of the membrane with 100% MeOH for 20 minutes at room temperature. The cells were stained with 0.5% crystal violet solution and several images of the wells were then taken and total number of cells counted for analysis.

Statistical Analysis.

Statistical significance evaluation of p-values was calculated using paired Student's t-test. A p-value of at least less than 0.05 is considered significant.

Example 3—Treatment of Castration Resistant Prostate Cancer: Docetaxel Sensitization by FOXC2 Inhibitor, MC-1-F2

Prostate cancer is one of the most diagnosed cancers worldwide, with androgen deprivation therapy (ADT) as the common prescribed treatment for advanced prostate cancer. However, ADT therapy leads to the acquisition of androgen-independent mechanisms, known as castration resistant prostate cancer (CRPC). The epithelial-mesenchymal transition (EMT) has emerged as a target for CRPC, with the transcription factor FOXC2 being a top candidate for EMT inhibition. Previous research into the inhibition of FOXC2 lead to the discovery of MC-1-F2, the first direct small molecule inhibitor of FOXC2. During the current study on CRPC, MC-1-F2 was able to show a decrease in EMT markers, inhibition of cancer stem cell properties and decrease in invasive capabilities in CRPC cell lines DU145 and PC3. A synergistic effect was also demonstrated between MC-1-F2 and docetaxel treatments. This lower dosage administration of docetaxel can lead to a delay in the development of chemoresistance, a main obstacle in the treatment of CRPC.

Prostate cancer is one of the top five most diagnosed cancers worldwide (Yun et al., 2016), with androgen deprivation therapy (ADT) as the common prescribed treatment for advanced prostate cancer (Li et al., 2014). However, ADT therapy leads to the acquisition of androgen-independent mechanisms (Paranjape et al., 2016). This resistance to ADT leads to what is known as castration resistant prostate cancer (CRPC), with about 90% (do Amaral, 2017) of patients diagnosed progressing to this stage. This stage of cancer progression is associated with distant metastasis (Montanari et al., 2017), androgen independence (Sun et al., 2012), and resistance to common chemotherapeutic agents such as docetaxel (Hwang, 2012). These characteristics lead to high mortality rates (Li et al., 2014) with survival rates of 1-2 years after recurrence or metastatic lesion detection (do Amaral, 2017).

Current research into treatments of CRPC aim at targeting the epithelial-mesenchymal transition (EMT). EMT leads to the breakdown of cell-cell contact (Lo et al., 2017), acquisition of cancer stem cell like characteristics, increase invasive capabilities and increase in chemoresistance (Figiel et al., 2017). EMT has emerged as a target for CRPC as most mortality associated events are due to distant metastasis (Wang et al., 2012). It has been suggested by a number of researchers that androgen maintenance is necessary for EMT regulation, with androgen deprivation leading to androgen independence causing an initiation of EMT (Li et al., 2014; Montanari et al., 2017). Thus, the main treatment of prostate cancer, ADT therapy, leads to EMT initiation and progression into CRPC.

Alternatives to ADT therapy for prostate cancer focus on the use of chemotherapeutic agents such as docetaxel (Jaworska et al., 2015). However, as stated before, chemoresistance develops over time. Chemoresistance in EMT is governed by the transcription factor ZEB1 (Paranjape et al., 2016), which is governed by FOXC2 (Wang et al., 2018). The transcription factor FOXC2, has been previously shown to a central regulator of EMT (Mani et al., 2008), with FOXC2 being necessary for the maintenance and initiation of EMT (Mani et al., 2008). It has also been shown that high FOXC2 levels are associated with CRPC, as well as vital in the induction of ADT resistance (Paranjape et al., 2016). The inhibition of FOXC2 was shown to inhibit EMT progression, render cells more susceptible to docetaxel, and lead to a decrease in cancer stem cell characteristics (Paranjape et al., 2016).

Previous research into the inhibition of FOXC2 lead to the discovery of MC-1-F2 (FIG. 25), the first direct small molecule inhibitor of FOXC2. MC-1-F2 was able to show a decrease in EMT markers, inhibition of cancer stem cell properties and decrease in invasive capabilities. The current study focuses on the use of MC-1-F2 in the treatment of CRPC to determine the effects of FOXC2 inhibition of CRPC and examine MC-1-F2's potential as a chemotherapeutic agent.

Due to our interest in CRPC the cell lines DU145 and PC3 were chosen due to their chemoresistance to high concentrations of enzalutamide, androgen independence, and relatively high expression of FOXC2 (FIGS. 30A&B). First, the effect of MC-1-F2 on the inhibition of EMT markers was examined (FIGS. 26A-G). As expected from previous studies, MC-1-F2 was able to inhibit various EMT markers such as ZEB1, Vimentin, N-cadherin and Slug in both PC3 and DU145. A recovery of the epithelial marker ZO-1 was also seen; however, no recovery in the expression levels of E-cadherin in PC3 cells was seen. There was a recovery of E-cadherin in DU145 cells. The variability in E-cadherin expression can be due to a different mode of action the ligand MC-1-F2 is having on prostate cancer cells, possibly a time dependent effect of the ligand. These results provided enough evidence to suggest that the ligand is having a similar effect on prostate cancer cell lines as previously reported with breast cancer cell lines with the inhibition of EMT progression.

After confirmation of the ligand's ability to block EMT, the ligand's ability to decrease cancer stem cell (CSC) characteristics was determined. CRPC is plagued by a higher ratio of CSC to normal prostate cells, leading to the acquired characteristics of higher proliferative and self-renewal capabilities (Yun et al., 2016). CSC markers, Nanog, C-myc and KLF4, were examined. All CSC markers showed significant decreases after treatment with 20 µM of MC-1-F2 in both cell lines (FIGS. 27A-D). FOXC2 has been shown to be required for CSC maintenance, thus these results correlate with data previously reported (Mani et al., 2008).

Following determination of both inhibition of EMT and CSC properties, the inhibition of the migratory and invasive capabilities of both cell lines following MC-1-F2 treatment was examined through the use of a transwell invasion assay. Cell lines PC3 and DU145 both showed remarkable inhibition in invasiveness after treatment with MC-1-F2 for 24 hours as compared to the DMSO condition (FIGS. 28A&B). The effect of MC-1-F2 was also tested on LNCaP, an androgen-dependent, low FOXC2 expression level cell line (FIGS. 31A&B) and saw to change in the number of invasive cells upon treatment. These results correlate with those studies done on metastatic breast cancer cell lines upon MC-1-F2 treatment. Collectively these results demonstrate that MC-1-F2 is able to inhibit EMT in CRPC, and in turn inhibit the CSC characteristics and the invasive properties of both PC3 and DU145.

Inhibition of EMT in CRPC could lead to a new form of therapeutics to aid once androgen-independence is achieved. However, in order for MC-1-F2 to be considered an effective chemotherapeutic agent, its $EC_{50}$ in prostate cancer needed to be determined as well as how it compares to other chemotherapeutic agents on the market and whether it is able to inhibit chemoresistance or lower the sensitivity of CRPC to commercially available drugs. In order to determine the $EC_{50}$ of MC-1-F2, an MTT assay on cell viability was performed in both DU145 and PC3. Although the effects of the drug were seen at 20 µM, the $EC_{50}$ for DU145 and PC3, respectively, are 48.14 µM and 46.65 µM (FIGS. 32A&B). These doses are higher than those encountered with breast cancer cell lines. This is most likely due to the lower FOXC2 expression levels founds in prostate cell lines when compared to the breast cell lines. MTT cell viability studies were also performed utilizing Enzalutamide (an AR agonist) and docetaxel (a commercially available chemotherapeutic drug) (FIGS. 33A&B). Enzalutamide showed no effect on both cell lines, as expected since both cell lines are androgen-independent. However, docetaxel had a potent effect on both cell lines with and $EC_{50}$ of 7.6 nM in PC3 and 6.1 nM in DU145.

Docetaxel is a commonly prescribed treatment for CRPC patients; however, some patients do not respond to therapy and chemoresistance inevitably develops (Hwang, 2012). Docetaxel acts in a similar manner to paclitaxel, another common chemotherapeutic drug. These drugs work by promoting microtubulin assembly and inhibiting microtubule dynamics, leading to mitotic progression impairment and cell cycle arrest (Herbst & Khuri, 2003). Docetaxel was shown to have great effects on the treatment of CRPC, but ultimately failed to be an effective treatment due to the acquisition of chemoresistance by most patients treated (Bissery, 1995). The cause of such resistance is not yet well understood. Combination drug treatments were carried out with enzalutamide or docetaxel and MC-1-F2, to determine if any synergistic effects existed. Although previous studies have shown that FOXC2 inhibition can restore androgen expression in androgen-independent cell lines (Paranjape et al., 2016), that effect was not observed in this study (FIGS. 34A&B). As such there was only additive effects between MC-1-F2 and enzalutamide treatment (FIGS. 35A&B). Although no synergism was seen, this can still be a prominent treatment in the early stages of prostate cancer, before androgen-independent mechanisms develop. However, synergistic effects were seen between MC-1-F2 and docetaxel treatment. The dose response curve showed synergistic effects induced after co-treatment, further validated by a negative combination index (FIGS. 29A&B). A combination index that is below zero is indicative of synergism, while above 0 is an additive effect. The synergism between MC-1-F2 and docetaxel is indicating that the ligand is sensitizing the cells further to the effects of docetaxel. The $EC_{50}$ of docetaxel in DU145 became 0.215 nM and 0.266 nM in PC3. This drop in the required dosage of docetaxel to achieve 50% inhibition can be a breakthrough for CRPC. A lower dosage administration of docetaxel can lead to the delay in the development of chemoresistance and fewer side effects for the patients. MC-1-F2 has also been shown to be able to halt invasive cells, making this combination of treatment adept at treating both primary and metastatic tumours, while possibly delaying the onset of chemoresistance plaguing CRPC. While it has been shown that FOXC2 inhibition leads to cell cycle arrest and reduction of proliferation (Gan et al., 2015) there is more to be studied about how it causes cell death. Thus, further experiments are underway to evaluate how MC-1-F2, causing FOXC2 inhibition, leads to cell death and how this causes synergism with the effects of docetaxel.

In this study on the effects of the ligand MC-1-F2 on CRPC, marked decreases in mesenchymal markers, CSC markers, and inhibition of invasive capabilities upon treatment were shown. This data strongly demonstrates the capability of MC-1-F2 to inhibit EMT progression in CRPC, apart from those results already seen in breast cancer. As the first direct small molecule inhibitor of FOXC2, MC-1-F2 can aid as an additive chemotherapeutic drug to common therapies already in use. Due to such thought process, combinatorial drug experiment were performed to test its effect on enzalutamide and docetaxel, two common drugs of choice for the treatment of CRPC. MC-1-F2 showed no effect on AR expression as previously reported in the literature. More studies need to be done on AR expression regulation by EMT and particularly by FOXC2. Overall, these studies provide a new method for the treatment of CRPC by sensitizing cells to docetaxel, lowering the required drug dosages necessary for effective treatment.

Example 4—Experimental Methods for Example 3

Synthesis of MC-1-F2.

100 mg of MBHA Rink Amide beads (Novabiochem) were swelled in DMF for 1 hour and followed by deprotection with 20% piperidine. After a full wash (3×DMF, 2×MeOH, 2×DCM, 3×DMF), 4,6-dichloro-N-(4-phenoxyphenyl)-1,3,5-triazin-2-amine (5 eq.) was added in dry NMP followed by DIPEA (10 eq.) and mixed at room temperature for 5 hours. Unless stated, all beads were subject to a full wash after each reaction step. 1-[(4-Nitrophenyl)sulfonyl]piperazine (5 eq.) in dry NMP with DIPEA (10 eq.) was added and reacted at 60° C. overnight. The beads were deprotected using DBU (10 eq.) and 2-mercaptoethanol (10 eq.) for 3 hours at room temperature. Followed was the addition of the 4,6-dichloro-N-[4-(4-morpholinyl)phenyl]-1,3,5-triazin-2-amine (5 eq.) in dry NMP and DIPEA (10 eq.) at 60'C for 5 hours. Followed by the addition of 1-(4-aminobutyl)guanidine (10 eq.) in dry NMP with DIPEA (20 eq.) at 60° C. overnight. The beads were cleaved and deprotected in TFA solution (95% TFA, 2.5% TIS, 2.5% H2O) for 2 hours. The resulting solution was concentrated and purified by column chromatography (DCM with 20% MeOH and 0.1% $NH_4OH$), affording a yellow solid product in 60% yield. 1H NMR (500 MHz DMSO-d6) δ (major, ppm) 7.68-7.55 (d, 2H), 7.55-7.35 (d, 2H), 7.44-7.30 (m, 2H), 7.12-7.05 (m, 1H), 6.86-6.98 (m, 4H), 6.82-6.89 (d, 2H), 3.72-3.73 (s, 4H), 3.41 (s, 8H), 3.16 (m, 4H), 3.02 (m, 4H), 1.48-1.53 (m, 2H), 1.20-1.23 (m, 2H). MALDI-TOF [M+H]+ 747.9 (calc. 746.9).

Synthesis of MC-C2.

100 mg of MBHA Rink Amide beads (Novabiochem) were swelled in DMF for 1 hour and followed by deprotection with 20% piperidine. After a full wash (3×DMF, 2×MeOH, 2×DCM, 3×DMF), 4,6-dichloro-N-(methyl)-1,3,5-Triazin-2-amine (5 eq.) was added in dry NMP followed by DIPEA (10 eq.) and mixed at room temperature for 5 hours. Unless stated all beads were subject to a full wash after each addition. 1-[(4-Nitrophenyl) sulfonyl]piperazine (5 eq.) in dry NMP with DIPEA (10 eq.) was added and reacted at 60° C. overnight. The beads were deprotected using DBU (10 eq.) and 2-mercaptoethanol (10 eq.) for 3 hours at room temperature. Followed was the addition of the 4,6-dichloro-N-(methyl)-1,3,5-triazin-2-amine (5 eq.) in dry NMP and DIPEA (10 eq.) at 60° C. for 5 hours. The beads were cleaved and deprotected in TFA solution (95% TFA, 2.5% TIS, 2.5% H2O) for 2 hours. The resulting solution was concentrated and purified by column chromatography (DCM with 3% MeOH and 0.1% $NH_4OH$), affording a white solid product in 65% yield. 1H NMR (500 MHz, CDCl3) δ (major, ppm) 3.32-3.37 (m, 8H), 2.69 (m, 3H), 2.72 (m, 3H). MALDI-TOF [M+H]+ 352.2 (calc. 351.8).

Cell Lines and Cell Culture.

PC3 and DU145 were cultured in RPMI 1640 medium. All cell culture media were supplemented with 10% bovine growth serum (BGS), 1% L-glutamine and 0.5% Penicillin/Streptomycin antibiotic, and the cultured cells were maintained in a 37° C. incubator with 5% $CO_2$. Cell culture media and supplements were purchased from Fisher Scientific unless otherwise indicated. Cell lines were purchased from American Type Culture Collection (ATTC).

Cell Viability Assay.

Cell viability was assessed by MTT (3-(4,5-Dimethylthiazol-2-yl)-2,5-Diphenyltetrazolium Bromide) assay 5,000 cells were seeded on a 96-well cell culture plate and were incubated for at least 24 hours prior to drug treatment. The MTT reagent (Fisher Scientific) was added to the culture medium 3 hours prior to the end of compound incubation. The reaction took place in the 37° C. incubator with 5% $CO_2$ for 3 hours. Cell culture medium was then removed from the wells. Cells with the insoluble purple formazan were lysed with DMSO for 10 mins at room temperature, 200 μL per well. Absorbance was read at 570 nm using a plate reader.

SDS-PAGE and Western Blot Analysis.

50 μg of total protein per sample was incubated with 4× loading buffer at 100° C. for 5 min. Protein samples were then loaded into a polyacrylamide gel and subjected to SDS-PAGE. Resolved proteins were then transferred by a wet transfer method to a PVDF membrane at 100 V for 1 hour using a BioRad Mini Trans-Blot Electrophoresis Transfer Cell. Upon the completion of wet transfer, the membrane was then blocked with 5% (w/v) fat-free milk in 1× Tris-buffered saline/0.1% (v/v) Tween-20 (TBS-T) for at least 1 hour. Then incubated with the respective primary antibodies diluted in 5% BSA in 1×TBST at 4° C. overnight. The following day exposed to 1:1000 dilution of anti-mouse or HRP-conjugated secondary antibodies in 5% (w/v) fat-free milk in 1×TBS-T for 1 hour at room temperature. The probed proteins were then detected for chemiluminescent signal using SuperSignal Chemiluminescent Substrate (PIERCE). Pierce antibodies: B-actin, and all other antibodies used are from cell signaling.

Transwell Invasion Assay.

Matrigel invasion chambers (Corning) were allowed to come to room temperature and allowed to rehydrate for 2 hours in a cell incubator. Cells were treated 24 hours prior to assay and starved in 2% FBS in DMEM for 2 hours prior to assay. A cell suspension containing 5×104 cells/mL was prepared. Chemoattractant (DMEM+10% FBS) was added to the bottom of the wells. Using forceps, the inserts were transferred inside the wells and 0.5 mL of cell suspension was immediately added. The chambers were incubated for 22 hours in a humidified tissue culture incubator. After the 22 hours, the non-invading cells were removed by scrubbing the surface of the membrane. The cells were fixated with 4% formaldehyde solution for 2 minutes at room temperature. Followed by permeabilization of the membrane with 100% MeOH for 20 minutes at room temperature. The cells were stained with 0.5% crystal violet solution and several images of the wells were then taken and total number of cells counted for analysis.

Co-Treatment MTT Assay (Chou et al., 2007).

MTT cell viability assay was carried out in a 96-well clear well plate. Cells were seeded with a density of 5,000 cells per 200 μL of media. The cells were incubated in a 37° C. incubator with 5% $CO_2$ overnight. The cells were then treated with various concentrations of drugs in DMSO, 2 μL per well for 24 hours. The drug solution in DMSO contained both combinatoric drugs to be used: either MC-1-F2 and docetaxel or MC-1-F2 and enzalutamide. The drug ratios between MC-1-F2 and Docetaxel or Enzalutamide remained constant for each concentration. Then the MTT reagent (Fisher Scientific) was added to the culture medium 3 hours prior to the end of compound incubation. Cell culture medium was then removed from the wells. Cells with the insoluble purple formazan were lysed with DMSO for 10 mins at room temperature, 200 µL per well. Followed by absorbance reading at 570 nm using a plate reader, all tests were carried out in triplicate.

Statistical Analysis.

Statistical significance evaluation of p-values was calculated using paired Student's t-test. A p-value of at least less than 0.05 is considered significant.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bachelder et al., *J. Cell. Biol.*, 168:29-33, 2005.
Beck & Blanpain, *Nature Reviews. Cancer*, 13:727-738, 2013.
Bissery, *European Journal of Cancer*, 31:S1-S6, 1995.
Chou & Martin, "CompuSyn software for drug combinations and for general dose effect analysis, and user's guide," ComboSyn Inc, Paramus, (NJ), 2005.
Dent et al., *Clin. Cancer Res.*, 13:4429-4434, 2007.
do Amaral, *EMJ*, 2:50-56, 2017.
Fang et al., *American Journal of Human Genetics*. 67:1382-1388, 2000.
Figiel et al., *Human Pathology*, 61:26-32, 2017.
Gan et al., *Journal of Lipid Research*, 56:1471-1480, 2015.
Golden & Cantley, *Oncogene*, 34:4702-4712, 2015.
Graham et al., *Breast Cancer Research and Treatment*, 123:139-147, 2010.
Herbst & Khuri, *Cancer Treatment Reviews*, 29:407-415, 2003.
Hollier et al., *Cancer Res.*, 73:1981-1992, 2013.
Hwang, *Therapeutic Advances in Medical Oncology*, 4:329-340, 2012.
Ivanov et al., *Mol. Cell. Biol.*, 33:3749-3761, 2013.
Jaworska et al., *International Journal of Molecular Sciences*, 16:27433-27449, 2015.
Kalluri & Weinberg, *J. Clin. Invest.*, 119:1420-1428, 2009.
Lamouille et al., *Nature Reviews. Molecular Cell Biology*, 15:178-196, 2014.
Lee et al., *The Journal of Cell Biology*, 172:973-981, 2006.
Li et al., *Am. J. Cancer. Res.*, 5:2022-2034, 2015.
Li et al., *Molecular Cancer*, 13:55, 2014.
Lim et al., *Breast Cancer Res. Treat.*, 150:19-29, 2015.
Lin et al., *Clin. Cancer Res.*, 19:6404-6418, 2013.
Lo et al., *International Journal of Molecular Sciences*, 18:2079, 2017.
Mani et al., *Cell*, 133:704-715, 2008.
Mitra et al., *Oncotarget*, 6:10697-10711, 2015.
Montanari et al., *Oncotarget*, 8:35376, 2017.
Moon & Lim, *Current Opinion it Chemical Biology*, 24:38-47, 2015.
Oh et al., *Proc. Natl. Acad. Sci. U.S.A.*, 111:11007-11012, 2014.
Pai et al., *Methods in Molecular Biology*, 1263:287-298, 2015.
Paranjape et al., *Oncogene*, 35:5963, 2016.
Ren et al., *International Journal of Oncology*, 43:1719-1729, 2013.
Sato et al., *Stem Cells*, 34:1997-2007, 2016.
Schmalhofer et al., *Cancer Metastasis Rev.*, 28:151-166, 2009.
Singh & Settleman, *Oncogene*, 29:4741-4751, 2010.
Sun et al., *Cancer Research*, 72:527-536, 2012.
Tsai & Yang, *Genes & Development*, 27:2192-2206, 2013.
Wang et al., *Asian Pac. J. Cancer Prev.*, 15:10621-10625, 2014.
Wang et al., *Clinica Chimica Acta*, 479:84-93, 2018.
Wang et al., *Discovery Medicine*, 13:135, 2012.
Ware et al., *Oncotarget*, 7:50507-50521, 2016.
Werden et al., *Oncogene*, 35:5977-5988, 2016.
Yu et al., *Oncogene*, 32:431-443, 2013
Yun et al., *Asian Journal of Urology*, 3:203-210, 2016.
Yun et al., *Clinical Cancer Research*, 22:670-679, 2016.
Zhang et al., *American Journal of Cancer Research*, 6:97-104, 2016.
Zhang et al., *Cell Cycle*, 14:481-487, 2015.

What is claimed is:

1. A compound of the formula:

(I)

[Chemical structure of compound (I)]

or a pharmaceutically acceptable salt thereof.

2. A pharmaceutical composition comprising an effective amount compound according to claim 1 and a pharmaceutically acceptable excipient.

3. The pharmaceutical composition of claim 2, wherein the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in crmes, in lipid compositions, via a catheter, via a lavage, via continuous infusion, via infusion, via inhalation, via injection, via local delivery, or via localized perfusion.

4. A method of treating breast cancer or prostate cancer in a patient in need thereof comprising administering to the patient a therapeutically effective amount of a compound according to claim 1.

5. The method of claim 4, wherein the cancer is breast cancer.

6. The method of claim 4, wherein the cancer is prostate cancer.

7. The method of claim 4, wherein said cancer is metastatic breast cancer or metastatic prostate cancer.

8. The method of claim 5, wherein said breast cancer is drug-resistant breast cancer.

9. The method of claim 6, wherein said prostate cancer is castration-resistant prostate cancer.

10. The method according to claim 4, wherein the method further comprises administering a second therapy.

11. The method of claim 10, wherein the second therapy is surgery, a second chemotherapeutic, radiotherapy, or immunotherapy.

12. The method according to claim 4, wherein the patient is a mammal.

13. The method of claim 12, wherein the patient is a human.

14. The method according to claim 4, wherein the compound is administered once.

15. The method according to claim 4, wherein the compound is administered two or more times.

* * * * *